United States Patent
Kulkarni et al.

(10) Patent No.: US 11,191,740 B2
(45) Date of Patent: *Dec. 7, 2021

(54) METHODS FOR TREATING INFLAMMATORY SKIN CONDITIONS

(71) Applicant: DR. REDDY'S LABORATORIES LTD., Telangana (IN)

(72) Inventors: Swati Kulkarni, Thane (IN); Bijay Kumar Padhi, Dist.-Ganjam (IN); Shanvas Alikunju, Hyderabad (IN); Rajeev Singh Raghuvanshi, South (IN); Srinivas Ramchandra Sidgiddi, West Windsor, NJ (US); Anirudh Gautam, Aesch (CH)

(73) Assignee: DR. REDDY'S LABORATORIES LTD., Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,754

(22) Filed: Jan. 7, 2019

(65) Prior Publication Data
US 2019/0209500 A1 Jul. 11, 2019

(30) Foreign Application Priority Data
Jan. 7, 2018 (IN) .............................. 201741023993

(51) Int. Cl.
| | |
|---|---|
| A61K 31/165 | (2006.01) |
| A61P 17/02 | (2006.01) |
| A61P 17/06 | (2006.01) |
| A61P 17/10 | (2006.01) |
| A61K 31/65 | (2006.01) |
| A61P 17/04 | (2006.01) |
| A61P 17/00 | (2006.01) |
| A61P 29/00 | (2006.01) |
| A61K 9/00 | (2006.01) |

(52) U.S. Cl.
CPC .......... *A61K 31/165* (2013.01); *A61K 9/0053* (2013.01); *A61K 31/65* (2013.01); *A61P 17/00* (2018.01); *A61P 17/02* (2018.01); *A61P 17/04* (2018.01); *A61P 17/06* (2018.01); *A61P 17/10* (2018.01); *A61P 29/00* (2018.01)

(58) Field of Classification Search
CPC .... A61K 31/165; A61K 31/65; A61K 9/0053; A61P 17/10; A61P 17/00; A61P 17/06; A61P 17/02; A61P 17/04; A61P 29/00
See application file for complete search history.

(56) References Cited

U.S. PATENT DOCUMENTS

| | | | |
|---|---|---|---|
| 7,008,631 B2 | 3/2006 | Ashley | |
| 7,790,705 B2 * | 9/2010 | Wortzman | A61K 31/65 514/152 |
| 8,252,776 B2 | 8/2012 | Wortzman et al. | |
| 8,603,506 B2 | 12/2013 | Ashley | |
| 8,945,516 B2 | 2/2015 | Tamarkin et al. | |
| 9,592,246 B2 | 3/2017 | Salman et al. | |
| 10,905,664 B2 | 2/2021 | Kulkarni et al. | |
| 2004/0147492 A1 | 7/2004 | Ashley | |
| 2009/0041846 A1 | 2/2009 | Wortzman et al. | |
| 2012/0093892 A1 | 4/2012 | Wortzman et al. | |
| 2017/0014517 A1 | 1/2017 | Tamarkin et al. | |
| 2020/0222345 A1 | 7/2020 | Kulkarni et al. | |

FOREIGN PATENT DOCUMENTS

| | | |
|---|---|---|
| EP | 2 221 056 A1 | 8/2010 |
| WO | 2002/080932 A1 | 10/2001 |
| WO | 2019135166 A1 | 7/2019 |

OTHER PUBLICATIONS

S. Ní Raghallaigh, et al., "Epidermal hydration levels in patients with rosacea improve after minocycline therapy" British Journal of Dermatology, vol. 171, Issue 2, pp. 259-266, Aug. 2014.
Jm Jackson, et al., "Efficacy of extended-release 45 mg oral minocycline and extended-release 45 mg oral minocycline plus 15% azelaic acid in the treatment of acne rosacea" J Drugs Dermatology, Mar.;12(3):292-8, 2013.
O Khokhar, et. al. "A case of granulomatous rosacea: Sorting granulomatous rosacea from other granulomatous diseases that affect the face" Dermatology Online Journal 10 (1): 6, 2004.
B Culp, et. al. "Rosacea: A Review" P&T: a peer-reviewed journal for formulary management, 34(1), 38-45, 2009.
HC Korting, et al. "Current topical and systemic approaches to treatment of rosacea" J Eur Acad Dermatol Venereol. Aug;23(8):876-82, 2009.
TA, CN, et. al. "Effects of minocycline on the ocular flora of patients with acne rosacea or seborrheic blepharitis" Cornea; 22(6):545-8, Aug. 2003.
AP Weinkle, et al. "Update on the management of rosacea" Clinical, Cosmetic and Investigational Dermatology; 8: 159-177, 2015.
W. Lee Fanning, et al. "Side effects of minocycline: a double-blind study" Antimicrobial Agents and Chemotherapy; 11(4): 712-717, 1977.
Jay A. Jacobson, et. al. "Vestibular reactions associated with minocycline" Antimicrobial Agents and Chemotherapy; 8(4): 453-456, 1975.
Joseph Frucht-Pery, et. al. "Efficacy of doxycycline and tetracycline in ocular rosacea" American Journal of Ophthalmology; 116:88-92, 1993.
Ping-Hsin Hung, et. al. "Minocycline-induced hyperpigmentation" The Journal of Family Practice; 41(2): 183-185, 1995.

(Continued)

*Primary Examiner* — Sahar Javanmard
(74) *Attorney, Agent, or Firm* — Squire Patton Boggs (US) LLP

(57) ABSTRACT

The present application relates to a method of treating an inflammatory skin condition by administering a pharmaceutical composition comprising a reduced dose of minocycline to a subject in need thereof, wherein said administration provides an effective plasma or interstitial fluid concentration of minocycline for treating the inflammatory skin condition.

18 Claims, 5 Drawing Sheets

(56) References Cited

OTHER PUBLICATIONS

Leanna J Perrei, et. al. "Non-antibiotic properties of tetracyclines and their clinical application in dermatology" Australasian Journal of Dermatology; 55: 111-118, 2014.

MINOCIN®—Label (Minocycline hydrochloride pellet-filled capsules—NDA No. 050649).

SOLODYN®—Label (Minocycline hydrochloride extended release tablets—NDA No. 050808).

DRACEA®—Label (Doxycycline capsules 40 mg—NDA No. 050805).

European Patent Office, International Search Report and Written Opinion issued in corresponding Application No. PCT/IB2019/000144, dated Jun. 17, 2019.

Leyden, James J., et al. "Clinical Considerations in the Treatment of Acne Vulgaris and Other Inflammatory Skin Disorders: a Status Report." Dermatologic CLI, Elsevier, USA, vol. 27, No. 1, Jan. 1, 2009, pp. 1-15.

Bikowski, J.B. "Subantimicrobial Dose Doxycycline for Acne and Rosacea," SKI, JACQ Communciations, Inc., Darien, LE, vol. 2, No. 4, Jul. 1, 2003, pp. 234-245.

Zouboulis, C.C., et al. "Update and Future of Systemic Acne Treatment." Dermato, S. Karger AG, CH, vol. 206, No. 1, Jan. 1, 2003, pp. 37-53.

* cited by examiner

Day 1

Day 21

Day 1

Day 21

METHODS FOR TREATING INFLAMMATORY SKIN CONDITIONS

RELATED APPLICATIONS

This application claims priority from Indian Patent Application No. IN 201741023993 filed Jan. 7, 2018, the entire disclosure of which is incorporated herein by this reference.

TECHNICAL FIELD

The present application relates to a method of treating an inflammatory skin condition by administering a pharmaceutical composition comprising a reduced dose of minocycline to a subject in need thereof, wherein said administration provides an effective plasma or interstitial fluid concentration of minocycline for treating said inflammatory skin condition.

BACKGROUND

Inflammatory skin conditions are those conditions of the skin in which inflammatory cells (e.g., polymorphonuclear neutrophils and lymphocytes) infiltrate the skin with no overt or known infectious etiology. Symptoms of inflammatory skin conditions generally include erythema (redness), edema (swelling), pain, pruritus, increased surface temperature and loss of function.

Rosacea is one such an inflammatory disorder of the skin which is characterized by inflammatory lesions of the skin that may resemble acne vulgaris papules and pustules ("acneform" lesions). It is a disorder of the superficial cutaneous vasculature resulting in erythema, accentuated flushing and telangiectasia and occurs predominantly in middle-aged adults and is virtually never observed in adolescents or young adults. Overall, rosacea is a type of inflammation that shows up as a rash, similar to other rashes/breakouts that cause an area of red, sensitive and inflamed skin. Such rashes are caused by irritation, allergies, infections, underlying diseases and structural defects of the skin, including blocked pores or malfunctioning oil glands. With time, people who have rosacea often see permanent redness in the center of their face. Rosacea related symptoms include, papules, pustules, blackheads, whiteheads or milia, nodules and cysts.

There are actually four different types of rosacea, although some people will have symptoms from more than one type at a time. The four types of rosacea are:
1. Erythematotelangiectatic rosacea: Redness, flushing, visible blood vessels,
2. Papulopustular rosacea: Redness, swelling, and acne-like breakouts,
3. Phymatous rosacea: Skin thickens and has a bumpy texture, redness and various symptoms from other subtypes, and
4. Ocular rosacea: Eyes red and irritated, eyelids can be swollen, and person may have what looks like a sty.

There are several subtypes of rosacea including, for example, but not limited to, pyoderma faciale (also known as rosacea fulminans), rosacea conglobate or phymatous rosacea.

Thus, a rosacea related disorder is any disorder which can occur in parallel with rosacea or be a contributing factor to the outbreak of rosacea or can resemble rosacea. Perioral dermatitis is an erythematous, papulopustular facial eruption that resembles rosacea and/or acne but typically starts around the nose.

Rosacea is a chronic inflammatory disorder characterized by facial flushing, telangiectasias, erythema, papules, pustules, and in severe cases, rhinophyma. Rosacea can be associated with the elevated levels of cathelicidins or with the elevated levels of a stratum corneum tryptic enzyme (SCTE). Rosacea includes any of the known types or subtypes classified in the art.

Acne is another such inflammatory disorder of the skin which is characterized by various types of lesions. The lesions associated with acne are usually categorized as either non-inflammatory or inflammatory. The spectrum of acne lesions ranges from non-inflammatory open or closed comedones; mild inflammatory acne lesions with comedones and few papules and pustules; moderate inflammatory acne lesions with comedones; several papules and pustules, and few nodules; or severe inflammatory acne lesions with comedones, several papules and pustules, multiple nodules, and scarring.

There are various treatment options available for inflammatory skin conditions like rosacea. It is treated with a variety of topical and/or therapies including topical and oral antibiotics, sodium sulfacetamide, and metronidazole.

Topical azelaic acid is an alternative to topical antibiotics to treat mild-to-moderate spots. However, some people find that it can cause side-effects such as burning, stinging, itching, scaling and dry skin.

When antibiotics are ineffective or poorly tolerated, oral isotretinoin may be effective, however, it has various side effects which is not suitable for everyone. Ivermectin cream is used occasionally for people with rosacea. It works by killing the mite *Demodex folliculorum* and also works to reduce some of the inflammation in the skin. Brimonidine gel is used to treat facial redness. It results in short-term vasoconstriction but has no effects on telangiectasia. Certain medications such as clonidine (an alpha2-receptor agonist) may reduce the vascular dilatation (widening of blood vessels) that results in flushing. Oral non-steroidal anti-inflammatory agents such as diclofenac may reduce the discomfort and redness of affected skin. Calcineurin inhibitors such as tacrolimus ointment and pimecrolimus cream are reported to help some subjects with rosacea. Other than medications, persistent telangiectasia has shown improvements with surgical treatments like vascular laser or intense pulsed light treatment. Papulopustular rosacea may also improve with laser treatment or radiofrequency. Other treatments like cautery, diathermy (electrosurgery) or sclerotherapy (strong saline injections) may also be helpful. Nutraceuticals targeting flushing, facial redness and inflammation may be beneficial.

Among various available treatment options, oral antibiotics like doxycycline is preferred, which reduces inflammation significantly. They reduce the redness, papules, pustules and eye symptoms of rosacea. The antibiotics are usually prescribed for 6 to 16 weeks, with the duration depending on the severity of the rosacea. Further courses are often needed from time to time, as the antibiotics don't cure the disorder. Sometimes other oral antibiotics such as cotrimoxazole or metronidazole are prescribed for resistant cases. Anti-inflammatory effects of antibiotics are under investigation and shown to inhibit matrix metalloproteinases function and in turn reduce cathelicidins and inflammation.

Currently in the United States of America, oral doxycycline is marketed under the brand name ORACEA®—40 mg once daily capsules—from Galderma Laboratories, approved by the US FDA in 2006. ORACEA® is indicated for the treatment of only inflammatory lesions (papules and pustules) of rosacea in adults. However, ORACEA® has well-known esophageal irritation and ulceration related side effects that really bother the subjects.

"MINOCIN®" which is a capsule comprising 50 mg, 75 mg or 100 mg of minocycline and approved for the treatment of various infections due to susceptible strains.

The usage of minocycline in higher strengths is associated with vestibular deregulation related adverse events like vertigo, incoordination or light-headedness. There is a clear void in the area of treating inflammatory skin conditions like rosacea in terms of safe and commercially approved minocycline dosage forms. And there is no approved dosage form of minocycline available for treating inflammatory skin conditions like rosacea.

There is a clear unmet need in the arts to provide alternatives for treatment for inflammatory skin conditions, which increase the opportunities for a greater number of individuals to achieve effective treatment. In this regard, there is a need for methods of providing an effective dose of minocycline for treatment of inflammatory skin conditions that maximizes therapeutic effect, while managing the adverse effects.

In other words, there is a need to provide minocycline dosage forms for better compliance to treat inflammatory skin conditions, which minimize the fluctuation or variance between peak and trough plasma or interstitial fluid levels of minocycline, with reduced side effects.

It is well known in the art that peak-to-trough fluctuations of drug concentration critically affect clinical response, tolerability and ultimately selection of appropriate drug and dosage forms required for treatment of inflammatory skin conditions.

Accordingly, the present application relates to a method of treating an inflammatory skin condition such as rosacea by administering a pharmaceutical composition comprising a reduced dose of minocycline comprising a therapeutically effective amount of minocycline to provide desired minocycline concentration in plasma and/or interstitial fluid for treating said inflammatory skin condition.

The present application provides a method of treating an inflammatory skin condition such as rosacea by administering a pharmaceutical composition comprising a reduced dose of minocycline to provide an effective treatment for said inflammatory skin condition.

The present application provides a method of treating an inflammatory skin condition such as acne by administering a pharmaceutical composition comprising a reduced dose of minocycline to provide an effective treatment for said inflammatory skin condition.

The present application also provides body-weight-independent dosing regimen for minocycline in a suitable pharmaceutical dosage form comprising a reduced dose of minocycline, as compared to other minocycline compositions for treating inflammatory skin conditions.

SUMMARY

In one embodiment, the present application relates to a method of treating an inflammatory skin condition by administering a composition comprising a reduced dose of minocycline.

In an aspect, the present application relates to a method of treating an inflammatory skin condition selected from, but not limited to, rosacea, acne, atopic dermatitis, folliculitis, perioral dermatitis, photo-damage, actinic keratosis, psoriasis, treatment of chronic wounds, bed sores, keratosis pilaris, surgical scars, acne scars, sebaceous cysts, inflammatory dermatoses, post inflammatory hyperpigmentation, xerosis, pruritis, lichen planus, nodular prurigo, eczema, and miliaria.

In another embodiment, the present application relates to a method of treating rosacea by administering a pharmaceutical composition comprising a reduced dose of minocycline.

In yet another embodiment, the present application relates to a method of treating acne by administering a pharmaceutical composition comprising a reduced dose of minocycline.

In another aspect of the above embodiments, the pharmaceutical composition of the present application comprises about 10 mg to 40 mg of minocycline.

In another embodiment, the present application relates to a method of treating an inflammatory skin condition by administering a pharmaceutical composition comprising an equivalent or a reduced dose of minocycline as compared to an oral doxycycline composition comprising 40 mg of doxycycline.

In another embodiment, the present application relates to a method of treating rosacea by administering a pharmaceutical composition comprising an equivalent or a reduced dose of minocycline as compared to an oral doxycycline composition comprising 40 mg of doxycycline.

In another embodiment, the present application relates to a method of treating acne by administering a pharmaceutical composition comprising an equivalent or a reduced dose of minocycline as compared to an oral doxycycline composition comprising 40 mg of doxycycline.

In another aspect of the above embodiments, the present application relates to a method of treating an inflammatory skin condition by administering an oral pharmaceutical composition comprising about 10 mg to 40 mg of minocycline to a subject in need thereof, wherein said administration results in an equivalent or improved efficacy as compared to an oral doxycycline composition comprising 40 mg of doxycycline.

In another aspect of the above embodiments, the present application relates to a method of treating rosacea by administering an oral pharmaceutical composition comprising about 10 mg to 40 mg of minocycline to a subject in need thereof, wherein said administration results in an equivalent or improved efficacy as compared to an oral doxycycline composition comprising 40 mg of doxycycline.

In an embodiment, the present application relates to a method of treating rosacea in a subject in need thereof, comprising selecting the subject for whom treatment with an oral doxycycline composition comprising 40 mg of doxycycline is effective or ineffective, and administering oral pharmaceutical composition comprising an equivalent or a reduced dose of minocycline.

In another embodiment, the present application relates to a method of treating rosacea in a subject in need thereof, comprising:
  (a) selecting the subject for whom treatment with an oral doxycycline composition comprising 40 mg of doxycycline is ineffective, and administering oral pharmaceutical composition comprising an equivalent or a reduced dose of minocycline; or
  (b) selecting the subject for whom treatment with an oral doxycycline composition comprising 40 mg of doxycycline is effective, and administering oral pharmaceutical composition comprising a reduced dose of minocycline.

In an aspect of the above embodiments, the composition of the present application comprises about 10 mg, about 20 mg, about 30 mg, or about 40 mg of minocycline.

In another aspect of the above embodiments, the method of treating rosacea reduces the severity of rosacea as compared to the severity of rosacea before the treatment, as assessed using Investigator's Global Assessment (IGA) scale.

In another aspect of the above embodiments, said method results in improved efficacy as assessed by the IGA score, in at least about 15%, 20%, 25%, 30%, 35%, 40%, 45%, 50%, 55%, 60%, 65%, 70% or 75% of the subjects as compared to the IGA score before the treatment.

In another aspect of the above embodiments, said method reduces the IGA score by at least about 25%, about 50%, about 75% or about 100% as compared to the IGA score following administration of an oral doxycycline composition comprising 40 mg of doxycycline.

In another aspect of the above embodiments, said method significantly reduces the number of inflammatory lesions as compared to the number of inflammatory lesions before the treatment.

In another aspect of the above embodiments, said method reduces the number of inflammatory lesions of the subject by at least about 15%, 20%, 25%, 30%, 35%, 40%, 45%, 50%, 55%, 60%, 65%, 70%, 80%, 85%, 90%, 95% or 100% as compared to the number of inflammatory lesions before the treatment.

In another aspect of the above embodiments, said method reduces the number of inflammatory lesions by at least about 15%, about 30%, about 50% or about 75% as compared to the number of inflammatory lesions following administration of an oral doxycycline composition comprising 40 mg of doxycycline.

In another aspect of the above embodiments, the composition of present application upon oral administration for about 3 weeks or less, exhibits maximum plasma concentration ($C_{maxSSP}$) of minocycline of not more than about 500 ng/ml.

In another aspect of the above embodiments, the composition of present application upon oral administration for about 3 weeks or less exhibits fluctuation index ($FI_{SSP}$) of about 0.9 to about 1.3 in plasma.

In another aspect of the above embodiments, the composition of present application upon oral administration for about 3 weeks or less exhibits at least about a 30% lower fluctuation index ($FI_{SSP}$) [$(C_{maxSSP}-C_{minSSP})/C_{avgSSP}$] in plasma, as compared to oral administration of a doxycycline composition comprising 40 mg of doxycycline.

In another aspect of the above embodiments, the composition of present application upon oral administration for about 3 weeks or less exhibits maximum plasma concentration ($C_{maxSSP}$) of at least about 10% lower as compared to oral administration of a doxycycline composition comprising 40 mg of doxycycline.

In another aspect of the above embodiments, the composition of present application upon oral administration for about 3 weeks or less exhibits at least about a 10% reduction in coefficient of variance (CV %) of maximum plasma concentration ($C_{maxSSP}$) as compared to oral administration of a doxycycline composition comprising 40 mg of doxycycline.

In another aspect of the above embodiments, the composition of present application upon oral administration for about 3 weeks or less exhibits at least about a 10% reduction in coefficient of variance (CV %) of minocycline exposure ($AUC_{0-tSSP}$) in plasma as compared to oral administration of a doxycycline composition comprising 40 mg of doxycycline.

In another aspect of the above embodiments, the composition of present application upon oral administration for about 3 weeks or less exhibits a plasma concentration ratio ($C_{maxSSP}:C_{maxP}$) of at least about a 30% lower ratio as compared to oral administration of a doxycycline composition comprising 40 mg of doxycycline.

In another aspect of the above embodiments, the composition of present application upon oral administration for about 3 weeks or less exhibits a plasma concentration ratio ($C_{maxSSP}:C_{maxP}$) of at least about 0.9.

In another aspect of the above embodiments, the composition of present application upon oral administration for about 3 weeks or less exhibits an average plasma concentration ($C_{avgSSP}$) of at least about 20% lower as compared to oral administration of a doxycycline composition comprising 40 mg of doxycycline.

In another aspect of the above embodiments, the composition of present application upon oral administration for about 3 weeks or less, exhibits ratio of minocycline exposure in interstitial fluid to plasma ($AUC_{0-tSSIF}/AUC_{0-tSSP}$) of at least about 10%, about 20%, about 30%, about 40% or about 50% higher as compared to oral administration of a doxycycline composition comprising 40 mg of doxycycline.

In another aspect of the above embodiments, the composition of present application upon oral administration for about 3 weeks or less, exhibits ratio of minocycline exposure in interstitial fluid to plasma ratio ($AUC_{0-tSSIF}/AUC_{0-tSSP}$) of at least about 10%, about 20%, about 30%, about 40% or about 50% higher as compared to oral administration of a doxycycline composition comprising 40 mg of doxycycline.

In another aspect of the above embodiments, the composition of present application comprising about 10 mg to about 40 mg dose of minocycline, upon oral administration for about 3 weeks or less exhibits at least one of the following pharmacokinetic parameters, when measured in plasma samples:

(a) $C_{maxSSP}/D$ of about 5 ng/ml/mg to about 12 ng/ml/mg; or (b) $AUC_{0-tSSP}/D$ of about 60 ng/ml/mg to about 114 ng/ml/mg.

In another aspect of the above embodiments, the composition of present application comprising about 10 mg to about 40 mg dose of minocycline, upon oral administration exhibits at least one of the following pharmacokinetic parameters, when measured in interstitial fluid samples:

(a) $C_{maxIF}/D$ of about 1.8 ng/ml/mg to about 3 ng/ml/mg; or (b) $AUC_{0-tIF}/D$ of about 25 ng/ml/mg to about 40 ng/ml/mg.

In an embodiment, the present application relates to a method of treating rosacea comprises administering a pharmaceutical composition comprising about 10 mg to about 40 mg of minocycline to a subject in need thereof.

In an aspect of the above embodiments, the pharmaceutical composition of present application is administered once daily.

In an aspect of the above embodiments, the pharmaceutical composition of present application is administered twice daily.

In another aspect of the above embodiments, the pharmaceutical composition of present application is with or without food.

In another aspect of the above embodiments, the pharmaceutical composition of present application is prepared in the form of oral tablets, capsules, pills, minitablets, pellets, granules, powder, suspension or syrup.

In an embodiment, the present application relates to a method of treating rosacea by administering oral pharmaceutical composition comprising a reduced dose of minocycline to a subject in need thereof, wherein said method provides body-weight-independent dosing regimen for minocycline.

In an embodiment, the present application relates to a method of preparing an oral pharmaceutical composition for treating an inflammatory skin condition in a subject in need thereof. In an embodiment, the method involves selecting and providing minocycline in the composition at an equivalent or a reduced dose of minocycline, as compared to an oral doxycycline composition comprising 40 mg of doxycycline. In an embodiment, the composition provides an equivalent or improved efficacy as compared to the oral doxycycline composition comprising 40 mg of doxycycline.

DESCRIPTION OF EXEMPLARY EMBODIMENTS

Figure 1A:
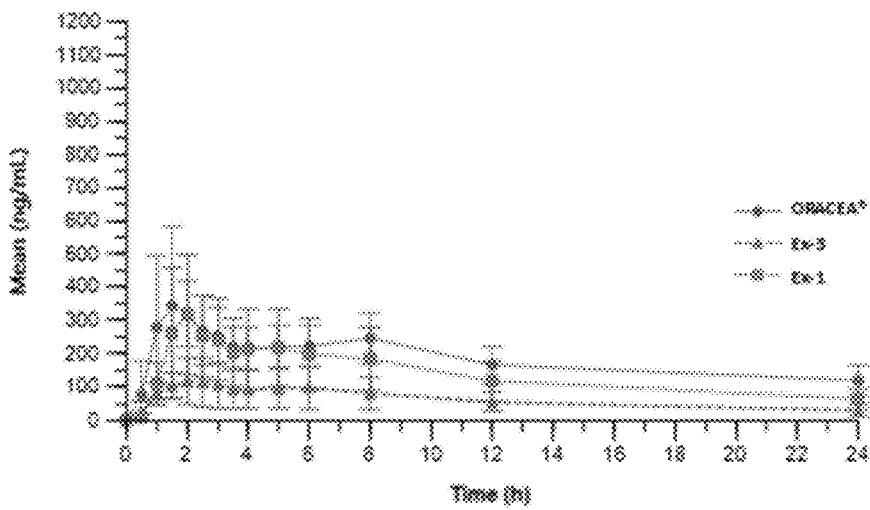
FIGS. 1A and 1B show mean plasma concentration for ORACEA®, Example 1 and Example 3 for day 1 and day 21 respectively, when subjected to an open-label, 6-cohort pharmacokinetic study.
Figure 1B:
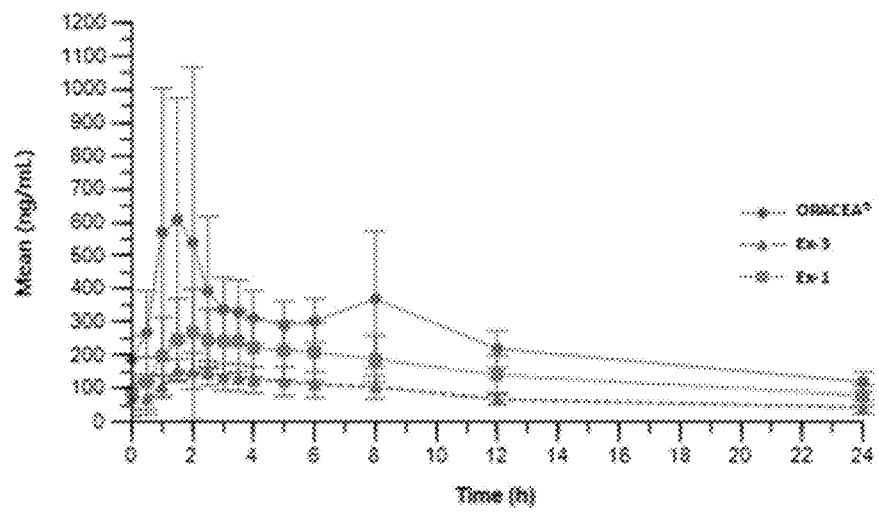
Figure 2A:
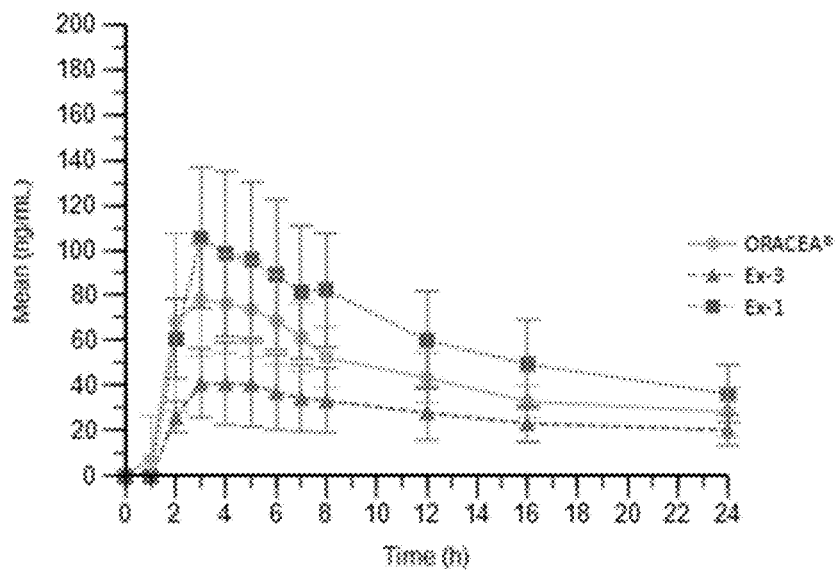
FIGS. 2A and 2B show mean interstitial fluid concentration for ORACEA®, Example 1 and Example 3 for day 1 and day 21 respectively, when subjected to an open-label, 6-cohort pharmacokinetic study.
Figure 2B:
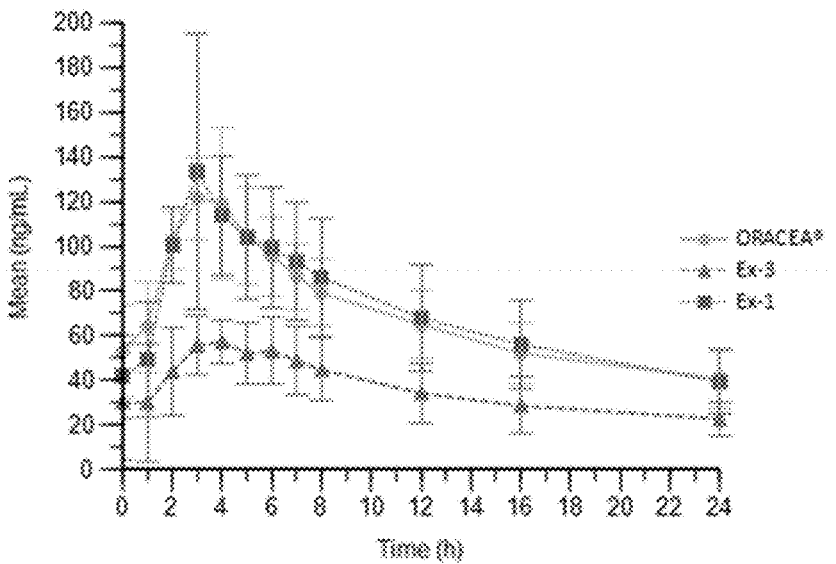

The details of one or more embodiments of the present invention are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Definitions

The terms as used herein have the following meanings:

The present invention can comprise or consist essentially of the components of the present invention as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. As used herein, "consisting of" means that the invention excludes additional elements, steps, or ingredients not specified in the claim.

The terms "a" and "the" as used herein, are understood to encompass the plural as well as the singular or otherwise clearly mentioned wherever needed. For example, reference to "an excipient" includes reference to one or more of such excipients, and reference to "the vehicle" includes reference to one or more of such vehicles.

The terms "about," "up to," "generally," and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

The term "about" is used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

The terms "composition" and "formulation" refer to a mixture of two or more compounds, elements, or molecules. Also this term may be used to refer to a mixture of one or more active agents with a pharmaceutically acceptable vehicle or excipients. Furthermore, the term "dosage form" can include one or more formulation(s) or composition(s) provided in a format for oral administration like tablets, capsules, pills, minitablets, pellets, granules, powder, suspension, syrup and the like or mixtures thereof.

As used herein, the terms "optional" or "optionally" mean that the subsequently described event or circumstance does or does not occur or exist and that the description includes instances where said event or circumstance occurs or exists, and instances where it does not.

As used herein, the terms "treatment" or "treating" that includes "alleviating," relate to curing or substantially curing a condition, as well as ameliorating at least one symptom of the condition, and are inclusive of prophylactic treatment and therapeutic treatment. As would be recognized by one or ordinary skill in the art, treatment that is administered prior to clinical manifestation of a condition then the treatment is prophylactic (i.e., it protects the subject against developing the condition). If the treatment is administered after manifestation of the condition, the treatment is therapeutic (i.e., it is intended to diminish, ameliorate, control, alleviate or maintain the existing condition and/or side effects associated with the condition). The terms relate to medical management of a subject with the intent to substantially cure, ameliorate, stabilize, or substantially prevent a condition, including but not limited to prophylactic treatment to preclude, avert, obviate, forestall, stop, or hinder something from happening, or reduce the severity of something happening, especially by advance action. As such, the terms treatment or treating include, but are not limited to: inhibiting the progression of a condition of interest; arresting or preventing the development of a condition of interest; reducing the severity of a condition of interest; ameliorating or relieving symptoms associated with a condition of interest; causing a regression of the condition of interest or one or more of the symptoms associated with the condition of interest; and preventing a condition of interest or the development of a condition of interest.

The term "minocycline" as used herein, is intended to include, but is not limited to, minocycline, its pharmaceutically acceptable salts, and pharmaceutically acceptable, pharmacologically active derivatives of minocycline, including both individual enantiomers of minocycline (dextrogyral and levogyral enantiomers) in their substantially pure form and their pharmaceutically acceptable salts, mixtures (in any ratio) of minocycline enantiomers and their pharmaceutically acceptable salts, and active metabolites of minocycline and their pharmaceutically acceptable salts. The chemical name of minocycline is [4S-(4α,4aα,5aα,12aα)]-4,7-Bis(dimethylamino)-1,4,4a,5,5a,6,11,12a-octahydro-3,10,12,12a-tetrahydroxy-1,11-dioxo-2-naphthacenecarboxamide. The solid state form of minocycline can be used. Alternatively, for example, minocycline can be amorphous or crystalline.

The term "doxycycline" as used herein, is intended to include, but is not limited to, doxycycline, its pharmaceutically acceptable salts, and pharmaceutically acceptable, pharmacologically active derivatives of doxycycline, including both individual enantiomers of doxycycline in their substantially pure form and their pharmaceutically acceptable salts, mixtures (in any ratio) of doxycycline enantiomers and their pharmaceutically acceptable salts, and active metabolites of doxycycline and their pharmaceutically acceptable salts. The chemical name of doxycycline is (4S,4aR,5S,5aR,6R,12aR)-4-(dimethylamino)-1,5,10,11,12a-pentahydroxy-6-methyl-3,12-dioxo-4a,5,5a,6-tetrahydro-4H-tetracene-2-carboxamide. The solid state form of doxycycline can be used. Alternatively, for example, doxycycline can be amorphous or crystalline.

The term "doxycycline composition" as used herein, includes an oral doxycycline marketed under the brand name as ORACEA®—40 mg once daily capsules—from Galderma Laboratories, approved by the US FDA with NDA No. 050805 and indicated for the treatment of only inflammatory lesions (papules and pustules) of rosacea in adults. The doxycycline composition includes ORACEA® or its pharmaceutical equivalents or its therapeutic equivalents or later approved drugs which are designated as AB rated by US FDA as per Approved Drug Products with Therapeutic Equivalence Evaluations (34th edition) or drugs obtained marketing approval by US FDA through Abbreviated New Drug Application (ANDA) filing by establishing bioequivalence.

The term "commercially available minocycline compositions" as used herein, includes oral minocycline marketed under the brand name as SOLODYN®—45 mg once daily tablets—from Medicis Pharmaceutical Corp., approved by the US FDA with NDA No. 050808 and indicated for the treatment treat only inflammatory lesions of non-nodular moderate to severe acne vulgaris in patients 12 years of age and older. The commercially available minocycline compositions includes SOLODYN® or its pharmaceutical equivalents or its therapeutic equivalents or later approved drugs which are designated as AB rated by US FDA as per Approved Drug Products with Therapeutic Equivalence Evaluations (34th edition) or drugs obtained marketing approval by US FDA through Abbreviated New Drug Application (ANDA) filing by establishing bioequivalence.

The term "pharmaceutically acceptable salts" as used herein, includes those salts which are, within the scope of sound medical judgment, suitable for use in contact with the tissues of humans and lower animals without undue toxicity, irritation, allergic response and the like, which are well known in the art. The salts can be prepared in situ during the final isolation and purification of the compounds of the invention, or separately by reacting the pharmaceutically active substance having a free base function with a suitable organic acid or inorganic acid. Examples of pharmaceutically acceptable salts include, but are not limited to, any of the salts or co-crystals of minocycline selected from hydrochloride, hydrobromide, sulphate, citrate, phosphate, maleate, formate, acetate, nitrate, mesylate, succinate, benzoate, and the like. The salts may be in solvate, hydrate, hemihydrates, or anhydrous forms.

The term "therapeutically effective amount" as used herein, refers to a prescribed amount of minocycline, which is less than 45 mg. In some embodiments, the therapeutically effective amount of minocycline is about 44 mg, about 43 mg, about 42 mg, about 41 mg, about 40 mg, about 39 mg, about 38 mg, about 37 mg, about 36 mg, about 35 mg, about 34 mg, about 33 mg, about 32 mg, about 31 mg, about 30 mg, about 29 mg, about 28 mg, about 27 mg, about 26 mg, about 25 mg, about 24 mg, about 23 mg, about 22 mg, about 21 mg, about 20 mg, about 19 mg, about 18 mg, about 17 mg, about 16 mg, about 15 mg, about 14 mg, about 13 mg, about 12 mg, about 11 mg, or about 10 mg. Such therapeutically effective amount provides a sufficient plasma and/or interstitial fluid concentration of minocycline for treating an inflammatory skin condition. The specified amount of minocycline is expected to be low enough to avoid serious side effects. The effective amount of minocycline and duration of the treatment will be based on the age and physical condition of the subject being treated, the severity of the condition, the nature of concurrent therapy, and like factors within the knowledge and expertise of the attending physician.

The term "reduced dose" refers to a dose of minocycline, wherein said dose comprises less than 45 mg of minocycline. In some embodiments, said reduced dose of minocycline comprises about 40 mg, about 35 mg, about 30 mg, about 25 mg, about 20 mg, about 15 mg or about 10 mg of minocycline. In some embodiments, the reduced dose of minocycline is about 44 mg, about 43 mg, about 42 mg, about 41 mg, about 40 mg, about 39 mg, about 38 mg, about 37 mg, about 36 mg, about 35 mg, about 34 mg, about 33 mg, about 32 mg, about 31 mg, about 30 mg, about 29 mg, about 28 mg, about 27 mg, about 26 mg, about 25 mg, about 24 mg, about 23 mg, about 22 mg, about 21 mg, about 20 mg, about 19 mg, about 18 mg, about 17 mg, about 16 mg, about 15 mg, about 14 mg, about 13 mg, about 12 mg, about 11 mg, or about 10 mg of minocycline. The term "reduced dose" can also be used herein to refer comparisons between minocycline and doxycycline. In this regard, minocycline that is provided at a reduced dose as compared to doxycycline is of a reduced mg amount. For example, less than 40 mg of minocycline is a reduced dose as compared to 40 mg doxycycline. Similarly, the term "equivalent dose" can be used to refer to comparisons between minocycline and doxycycline. In this regard, minocycline that is provided at an equivalent dose as compared to doxycycline is of the same mg amount. For example, 40 mg of minocycline is an equivalent dose to 40 mg doxycycline.

The term "sub-antimicrobial dose" refers to an amount having no significant antimicrobial effect on the body upon administration of such amount.

The term, "inflammatory skin condition" as used herein, refers to a condition resulting in inflammatory lesions characterized by rosacea, acne, atopic dermatitis, folliculitis, perioral dermatitis, photo-damage, actinic keratosis, psoriasis, treatment of chronic wounds, bed sores, keratosis pilaris, scars including surgical and acne scars, sebaceous cysts, inflammatory dermatoses, post inflammatory hyperpigmentation, xerosis, pruritis, lichen planus, nodular prurigo, eczema, or miliaria.

The term "rosacea" as used herein, includes a skin condition comprising inflammatory lesions (papulopustular rosacea—papules, pustules and nodules), vascular instability and/or vascular ectasia (erythematotelangiectatic rosacea), edema, skin thickening and/or rhinophyma changes (phymatous rosacea), acne rosacea, or ocular changes (ocular rosacea), wherein the full scope of rosacea, including its causes, symptoms, and effects as described by National Rosacea Society, which is a 501(c) (3) organization in the United States.

The term "acne" as used herein, includes a skin condition comprising all known types of acne, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstrual acne, acne pustulosa, acne scorbutica, acne scrofulosorum, acne urticata, acne varioliformis, acne venenata, propionic acne, acne excoriee, gram negative acne, steroid acne, and nodulocystic acne.

The term "subject" as used herein, refers to a human individual who may or may not be suffering from an inflammatory skin condition, who is a recipient of an oral pharmaceutical composition described herein.

The term "patient" as used herein, refers to a human individual who is suffering from an inflammatory skin condition, who is a recipient of the an oral pharmaceutical composition described herein.

The term "efficacy" refers to a reduction or inhibition of severity of an inflammatory skin condition such as rosacea, wherein said severity is assessed by counting inflammatory lesions, including papules, pustules and/or nodules, before the onset of treatment; and counting inflammatory lesions after treatment has been initiated; and assessing changes in an investigator's global assessment (IGA) score and/or in the number of inflammatory lesions. If desired, efficacy can be quantified by reduction of inflammatory lesion count from the baseline before treatment, by an improvement from the baseline in an IGA score, or by both the reduction of inflammatory lesion count and the IGA score. As used herein, the term "treatment success" can refer to a finding of efficacy.

The term "equivalent efficacy" refers to comparative treatment using two different compositions, wherein the resulting efficacy is substantially the same. For example, if treatment with two different compositions for the same period of time results in substantially the same reduction in the number of lesions, the compositions can be said to have equivalent or comparable efficacy.

The term "improved efficacy" refers to comparative treatment using two different compositions, wherein the resulting efficacy of one composition is greater as compared to another composition. For example, if treatment with a first composition and a second composition for the same period of time results in greater reduction in the number of inflammatory lesions for the second composition as compared to the first composition, the second composition is said to have improved efficacy as compared to the first composition.

The term "substantially" can be used to modify a term or value such that it is not an absolute. The term will be defined by the circumstances and the terms that it modifies, as those terms are understood by those skilled in the art. The term is indicative of an approximation or some amount of deviation, rather than perfect and absolute. For example, as will be recognized by those skilled in the art, when the term "substantially prevent" is used in connection with a prophylactic treatment, it should not be understood as an absolute term that would preclude any sign of any skin condition in a subject. Rather, as used in the context of prophylactic treatment, the term "substantially prevent" can refer to inhibiting the development of a skin condition, such as in a subject who may be predisposed to the skin condition but who has not yet been diagnosed as having it, limiting the severity of the developed skin condition, arresting the development of a skin condition, and the like.

The term "An investigator's global assessment (IGA) score" as used herein is determined by a trained medical professional evaluating the skin condition of a subject utilizing an investigative global assessment of the skin condition. Typically, such global assessments assign a value to the degree of rosacea exhibited by the skin. In addition to the assessment made by the medical professional, the subject's input and observations of their skin condition and responses to various inquiries (e.g., stinging or burning sensations) also play a role in determining the IGA score that is assigned. For example, the IGA score for rosacea (Table 1) can range from 0 (clear) to 1 (almost clear) to 2 (mild) to 3 (moderate) to 4 (severe).

TABLE 1

| Grade | Score | Clinical description |
|---|---|---|
| Clear | 0 | No inflammatory lesions present |
| Almost clear | 1 | Very few small papules, pustules |
| Mild | 2 | Few small papules pustules |
| Moderate | 3 | Several Small or large papules, pustules |
| Severe | 4 | Numerous Small and/or large papules, pustules |

The reduction in inflammatory lesion count is determined at each study visit inter alia by an absolute inflammatory lesion count or by a percentage change in inflammatory lesion count. The improvement assessment includes grading or scoring rosacea severity based on the total count or number of inflammatory lesions.

The term "moderate to severe rosacea" refers to at least about 10 papulopustular lesions before treatment. For example, the subject can have an IGA score of rosacea of about 3 or about 4, and at least about 10, 12, 15, 20, 25 or more inflammatory papulopustular lesions before treatment. As used herein, a subject having "moderate rosacea" has an IGA score of rosacea of about 3. As used herein, a subject having "severe rosacea" has an IGA score of rosacea of about 4.

The term "interstitial fluid" as used herein refers to the extracellular fluid that is located outside blood vessels and in spaces between the tissue cells, and does not contain blood and blood cells, but may contain non-cellular blood components.

The term "steady state" as used herein refers to a concentration level of minocycline in which there is no further difference, or having minimal difference, between the peak and trough concentrations of minocycline, in plasma or interstitial fluid. Thus, at steady state, the plasma or interstitial fluid concentration level of minocycline does not substantially fluctuate within the dosing interval after repeated doses of the formulation. The steady state is achieved in about 3 weeks or less, upon once or twice daily repeated dosing of the present pharmaceutical composition comprising minocycline. In certain situations steady state may be achieved in about 4 weeks.

The term "$C_{maxP}$" refers to the maximum plasma concentration.

The term "$C_{maxIF}$" refers to the maximum interstitial fluid concentration.

The term "$C_{minP}$" refers to the minimum plasma concentration.

The term "$C_{minIF}$" refers to the minimum interstitial fluid concentration.

The term "$C_{maxSSP}$" refers to the maximum plasma concentration achieved at steady state.

The term "$C_{maxSSIF}$" refers to the maximum interstitial fluid concentration achieved at steady state.

The term "$C_{minSSP}$" refers to the minimum plasma concentration achieved at steady state.

The term "$C_{minSSIF}$" refers to the minimum interstitial fluid concentration achieved at steady state.

The term "$C_{maxP}$/Dose" or "$C_{maxP}$/D" refers to the dose-normalized maximum plasma concentration.

The term "$C_{maxIF}$/Dose" or "$C_{maxIF}$/D" refers to the dose-normalized maximum interstitial fluid concentration.

The term "$C_{maxSSP}$/Dose" or "$C_{maxSSP}$/D" refers to the dose-normalized maximum plasma concentration achieved at steady state.

The term "$C_{maxSSIF}$/Dose" or "$C_{maxSSIF}$/D" refers to the dose-normalized maximum interstitial fluid concentration achieved at steady state.

The term "$C_{avgP}$" refers to the average concentration of minocycline in plasma within a 24 hour dosing interval exhibited by administration of the composition. $C_{avgP}$ is calculated as, $$C_{avgP} = \frac{AUC_{0-tP}(AUC \text{ over at } = 24 \text{ hour interval in plasma})}{\text{Dosing interval } (t = 24)}$$

The term "$C_{avgIF}$" refers to the average concentration of minocycline in interstitial fluid within a 24 hour dosing interval exhibited by administration of the composition. $C_{avgIF}$ is calculated as, $$C_{avgIF} = \frac{AUC_{0-tIF}(AUC \text{ over at } = 24 \text{ hour interval in interstitial fluid})}{\text{Dosing interval } (t = 24)}$$

The term "$C_{avgSSP}$" refers to the average concentration of minocycline in plasma within a 24 hour dosing interval exhibited by administration of the composition. $C_{avgSS}$ is calculated as, $$C_{avgSSP} = \frac{AUC_{0-tSSP} \, (AUC \text{ over at } = 24 \text{ hour interval at steady state in plasma})}{\text{Dosing interval } (t = 24)}$$

The term "$C_{avgSSIF}$" refers to the average concentration of minocycline in interstitial fluid within a 24 hour dosing interval exhibited by administration of the composition. $C_{avgSSIF}$ is calculated as, $$C_{avgSSIF} = \frac{AUC_{0-tSSIF} \, (AUC \text{ over at } = 24 \text{ hour interval at steady state in interstitial fluid})}{\text{Dosing interval } (t = 24)}$$

The term "$AUC_{0-tP}$" refers to the area under the plasma concentration-time curve; or minocycline exposure from time zero to time t, where "t" is the last sampling time point with measurable drug concentration.

The term "$AUC_{0-tIF}$" refers to the area under the interstitial fluid concentration-time curve; or minocycline exposure from time zero to time t, where "t" is the last sampling time point with measurable drug concentration.

The term "$AUC_{0-tSSP}$" refers to the area under the plasma concentration-time curve; or minocycline exposure from time zero to time t, where "t" is the last sampling time point with measurable drug concentration at steady state.

The term "$AUC_{0-tSSIF}$" refers to the area under the interstitial fluid concentration-time curve; or minocycline exposure from time zero to time t, where "t" is the last sampling time point with measurable drug concentration at steady state.

The term "$AUC_{0-tP}$/Dose" or "$AUC_{0-tP}$/D" refers to the dose-normalized area under the plasma concentration-time curve from time zero to time t, where "t" is the last sampling time point with measurable drug concentration.

The term "$AUC_{0-tIF}$/Dose" or "$AUC_{0-tIF}$/D" refers to the dose-normalized area under the interstitial fluid concentration-time curve from time zero to time t, where "t" is the last sampling time point with measurable drug concentration.

The term "$AUC_{0-tSSP}$/Dose" or "$AUC_{0-tSS}$/D" refers to the dose-normalized area under the plasma concentration-time curve from time zero to time t, where "t" is the last sampling time point with measurable drug concentration at steady state.

The term "$AUC_{0-tSSIF}$/Dose" or "$AUC_{0-tSS}$/D" refers to the dose-normalized area under the interstitial fluid concentration-time curve from time zero to time t, where "t" is the last sampling time point with measurable drug concentration at steady state.

The term "coefficient of variation (CV)" refers to the ratio of standard deviation to that of the mean value obtained from clinical data. It shows the extent of variability in relation to the mean value of the study population. The CV is expressed as a percentage (%) and lower the % CV, more precise is the data.

The term "fluctuation index ($FI_P$ or $FI_{SSP}$)" or "degree of fluctuation ($DOF_P$)" refers a measurement of variation in drug plasma level upon administration, over the course of a dosing interval or at steady state. The closer the fluctuation index to one, there is less variance over the course of a dosing period. Thus a reduced "$FI_P$ or $FI_{SSP}$" signifies that the difference in peak and trough plasma levels has been reduced. It is expressed as a ratio of maximum concentration to minimum concentration following administration according to the recommended dosing interval and calculated as, Fluctuation index $(FI_P) = [C_{maxP} - C_{minP}]/C_{avgP}$, or Fluctuation index $(FI_{SSP}) = [C_{maxSSP} - C_{minSSP}]/C_{avgSSP}$ The term "fluctuation index ($FI_{IF}$ or $FI_{SSIF}$)" or "degree of fluctuation ($DOF_{IF}$)" refers a measurement of variation in drug interstitial fluid level upon administration, over the course of a dosing interval or at steady state. The closer the fluctuation index to one, there is less variance over the course of a dosing period. Thus a reduced "$FI_{IF}$ or $FI_{SSIF}$" signifies that the difference in peak and trough interstitial fluid levels has been reduced. It is expressed as a ratio of maximum concentration to minimum concentration following administration according to the recommended dosing interval and calculated as, Fluctuation index ($FI_{IF}$)=[$C_{maxIF}$−$C_{minP}$]/$C_{avgIF}$, or Fluctuation index ($FI_{SSIF}$)=[$C_{maxSSIF}$−$C_{minSSIF}$]/$C_{avgSSIF}$ Oral tetracycline compounds are known for treating inflammatory skin conditions like rosacea. However, their higher doses and repeated administration with higher degree of fluctuation index or variations between peak and trough plasma, affects the treatment regimen with higher incidence of side effects. Having a treatment option with a reduced dose, lesser fluctuation index or variance between peak and trough plasma is long felt need.

The presently-disclosed invention is based, in part, on the surprising discoveries disclosed herein. Unexpectedly, minocycline exhibits comparative treatment results in % reduction in lesion counts for minocycline (about 40 mg), which is about 100% more as compared to doxycycline (40 mg) for equivalent doses. Additionally, % reduction in lesion counts for minocycline (about 20 mg) at a half dose is equivalent or greater than as compared to doxycycline (40 mg) at a whole dose.

Furthermore, as evidenced by comparative data, minocycline has improved efficacy for treating rosacea as compared to doxycycline at an equivalent dose, and has equivalent efficacy at a half dose.

Accordingly, the present application relates to a method of treating an inflammatory skin condition with a reduced dose of minocycline.

In an embodiment, the present application relates to a method of treating an inflammatory skin condition such as rosacea with a reduced dose of minocycline.

In an embodiment, the present application relates to a method of treating an inflammatory skin condition such as acne with a reduced dose of minocycline.

In another embodiment, the present application relates to a method of treating an inflammatory skin condition with a reduced dose of minocycline to provide an equivalent or improved efficacy as compared to an oral doxycycline composition comprising 40 mg of doxycycline.

In an embodiment, the present application relates to a method of treating rosacea by administering an oral pharmaceutical composition comprising a reduced dose of minocycline to a subject in need thereof, wherein said administration results in an equivalent or improved efficacy as compared to an oral doxycycline composition comprising 40 mg of doxycycline.

In an embodiment, the present application relates to a method of treating an inflammatory skin condition by selecting and administering an oral pharmaceutical composition comprising an equivalent or a reduced dose of minocycline, as compared to an oral doxycycline composition comprising 40 mg of doxycycline, to a subject in need thereof.

In an embodiment, the present application relates to a method of treating a rosacea by selecting and administering an oral pharmaceutical composition comprising an equivalent or a reduced dose of minocycline, as compared to an oral doxycycline composition comprising 40 mg of doxycycline, to a subject in need thereof.

In an embodiment, the present application relates to a method of treating an inflammatory skin condition in a subject which involves:
(a) selecting the subject for whom treatment with an oral doxycycline composition comprising 40 mg of doxycycline is ineffective, and administering an oral pharmaceutical composition comprising an equivalent or a reduced dose of minocycline; or
(b) selecting the subject for whom treatment with an oral doxycycline composition comprising 40 mg of doxycycline is effective, and administering an oral pharmaceutical composition comprising a reduced dose of minocycline.

In an embodiment, the present application relates to a method of treating rosacea in a subject in need thereof, comprising selecting the subject for whom treatment with an oral doxycycline composition comprising 40 mg of doxycycline is ineffective, and administering an oral pharmaceutical composition comprising an equivalent or a reduced dose of minocycline.

In an embodiment, the present application relates to a method of treating rosacea in a subject in need thereof, comprising selecting the subject for whom treatment with an oral doxycycline composition comprising 40 mg of doxycycline is ineffective, and administering an oral pharmaceutical composition comprising an equivalent dose of minocycline.

In an embodiment, the present application relates to a method of treating rosacea in a subject in need thereof, comprising selecting the subject for whom treatment with an oral doxycycline composition comprising 40 mg of doxycycline is ineffective, and administering an oral pharmaceutical composition comprising a reduced dose of minocycline.

In another embodiment, the present application relates to a method of treating rosacea in a subject in need thereof, comprising selecting the subject for whom treatment with an oral doxycycline composition comprising 40 mg of doxycycline is effective, and administering an oral pharmaceutical composition comprising an equivalent or a reduced dose of minocycline.

In another embodiment, the present application relates to a method of treating rosacea in a subject in need thereof, comprising selecting the subject for whom treatment with an oral doxycycline composition comprising 40 mg of doxycycline is effective, and administering an oral pharmaceutical composition comprising an equivalent dose of minocycline.

In another embodiment, the present application relates to a method of treating rosacea in a subject in need thereof, comprising selecting the subject for whom treatment with an oral doxycycline composition comprising 40 mg of doxycycline is effective, and administering an oral pharmaceutical composition comprising a reduced dose of minocycline.

In yet another embodiment, the present application relates to a method of treating rosacea in a subject in need thereof, comprising:
(a) selecting the subject for whom treatment with an oral doxycycline composition comprising 40 mg of doxycycline is ineffective, and administering an oral pharmaceutical composition comprising an equivalent or a reduced dose of minocycline; or (b) selecting the subject for whom treatment with an oral doxycycline composition comprising 40 mg of doxycycline is effective, and administering an oral pharmaceutical composition comprising an equivalent or a reduced dose of minocycline.

In an embodiment, the present application relates to a method of preparing an oral pharmaceutical composition for treating an inflammatory skin condition in a subject in need thereof, comprising selecting and providing minocycline in said composition at an equivalent or reduced dose, as compared to an oral doxycycline composition comprising 40 mg of doxycycline.

In an embodiment, the present application relates to a method of preparing an oral pharmaceutical composition for treating rosacea in a subject in need thereof, comprising selecting and providing minocycline in said composition at an equivalent or reduced dose, as compared to an oral doxycycline composition comprising 40 mg of doxycycline.

In an embodiment, the present application relates to a method of preparing an oral pharmaceutical composition for treating an inflammatory skin condition in a subject in need thereof, comprising selecting and providing minocycline in said composition at an equivalent or reduced dose, as compared to an oral doxycycline composition comprising 40 mg of doxycycline, wherein said composition provides equivalent or improved efficacy as compared to the oral doxycycline composition comprising 40 mg of doxycycline.

In an embodiment, the present application relates to a method of preparing an oral pharmaceutical composition for treating rosacea in a subject in need thereof, comprising selecting and providing minocycline in said composition at an equivalent or reduced dose, as compared to an oral doxycycline composition comprising 40 mg of doxycycline, wherein said composition provides equivalent or improved efficacy as compared to the oral doxycycline composition comprising 40 mg of doxycycline.

In an aspect of the above embodiments, the pharmaceutical composition comprises less than 45 mg of minocycline.

In another aspect of the above embodiments, the pharmaceutical composition comprises from about 10 mg to about 40 mg of minocycline.

In another aspect of the above embodiments, the method of preparing an oral pharmaceutical composition comprising minocycline, wherein said composition comprises from about 10 mg to about 40 mg of minocycline.

In another aspect of the above embodiments, the pharmaceutical composition comprises about 10 mg of minocycline.

In another aspect of the above embodiments, the pharmaceutical composition comprises about 20 mg of minocycline.

In another aspect of the above embodiments, the pharmaceutical composition comprises about 30 mg of minocycline.

In another aspect of the above embodiments, the pharmaceutical composition comprises about 40 mg of minocycline.

In an embodiment, the present application relates to a method of treating rosacea by administering an oral pharmaceutical composition comprising a reduced dose of minocycline to a subject in need thereof, wherein said composition exhibits plasma concentration sufficient to reduce the severity of an inflammatory skin condition.

In an embodiment, the present application relates to a method of treating rosacea by administering an oral pharmaceutical composition comprising a reduced dose of minocycline to a subject in need thereof, wherein said composition exhibits plasma concentration sufficient to reduce the severity of an inflammatory skin condition such as rosacea.

In an embodiment, the present application relates to a method of treating rosacea by administering an oral pharmaceutical composition comprising a reduced dose of minocycline to a subject in need thereof, wherein said composition exhibits plasma concentration sufficient to reduce the severity of an inflammatory skin condition such as acne.

In an aspect of the above embodiments, the present application relates to a method of treating an inflammatory skin condition by administering a pharmaceutical composition comprising a reduced dose of minocycline to a subject in need thereof, wherein said composition exhibits a maximum plasma concentration ($C_{maxP}$) of not more than about 500 ng/ml of minocycline upon administration, to reduce the severity of an inflammatory skin condition.

In an aspect of the above embodiments, the present application relates to a method of treating rosacea by administering a pharmaceutical composition comprising a reduced dose of minocycline to a subject in need thereof, wherein said composition exhibits a maximum plasma concentration ($C_{maxP}$) of not more than about 500 ng/ml of minocycline upon administration, to reduce the severity of rosacea.

In an aspect of the above embodiments, the present application relates to a method of treating acne by administering a pharmaceutical composition comprising a reduced dose of minocycline to a subject in need thereof, wherein said composition exhibits a maximum plasma concentration ($C_{maxP}$) of not more than about 500 ng/ml of minocycline upon administration, to reduce the severity of acne.

In an aspect of the above embodiments, the present application relates to a method of treating inflammatory skin condition by administering a pharmaceutical composition comprising a reduced dose of minocycline to a subject in need thereof, wherein said composition exhibits a maximum plasma concentration ($C_{maxP}$) of not more than about 500 ng/ml, about 450 ng/ml, about 440 ng/ml or about 430 ng/ml of minocycline upon administration, to reduce the severity of an inflammatory skin condition.

In an aspect of the above embodiments, the present application relates to a method of treating rosacea by administering a pharmaceutical composition comprising a reduced dose of minocycline to a subject in need thereof, wherein said composition exhibits a maximum plasma concentration ($C_{maxP}$) of not more than about 500 ng/ml, about 450 ng/ml, or about 440 ng/ml or about 430 ng/ml of minocycline upon administration, to reduce the severity of rosacea.

In an aspect of the above embodiments, the present application relates to a method of treating acne by administering a pharmaceutical composition comprising a reduced dose of minocycline to a subject in need thereof, wherein said composition exhibits a maximum plasma concentration ($C_{maxP}$) of not more than about 500 ng/ml, about 450 ng/ml, about 440 ng/ml or about 430 ng/ml of minocycline upon administration, to reduce the severity of acne.

Oral tetracycline compounds are known for treating inflammatory skin conditions like rosacea. However, their higher doses and repeated administration with higher degree of fluctuation index or variations between peak and trough plasma, affects the treatment regimen with higher incidence of side effects. Having a treatment option with lesser fluctuation index or variance between peak and trough plasma is long felt need.

Accordingly, the present application relates to a method of treating an inflammatory skin condition with lower fluctuation index, may be leading to lesser incidence of side effects.

In one embodiment, the present application relates to a method of treating an inflammatory skin condition by administering a pharmaceutical composition comprising a therapeutically effective amount of minocycline to a subject in need thereof, wherein said composition upon oral administration exhibits a lower fluctuation index ($FI_P$) [$(C_{maxP}-C_{minP})/C_{avgP}$] in plasma.

In one embodiment, the present application relates to a method of treating an rosacea by administering a pharmaceutical composition comprising a therapeutically effective amount of minocycline to a subject in need thereof, wherein said composition upon oral administration exhibits a substantially lower fluctuation index ($FI_P$) [$(C_{maxP}-C_{minP})/C_{avgP}$] in plasma.

In one embodiment, the present application relates to a method of treating an acne by administering a pharmaceutical composition comprising a therapeutically effective amount of minocycline to a subject in need thereof, wherein said composition upon oral administration exhibits a substantially lower fluctuation index ($FI_P$) [$(C_{maxP}-C_{minP})/C_{avgP}$] in plasma.

In another embodiment, the present application relates to a method of treating an inflammatory skin condition by administering a pharmaceutical composition comprising a therapeutically effective amount of minocycline to a subject in need thereof, wherein said composition upon oral administration exhibits a lower fluctuation index ($FI_{SSP}$) [$(C_{maxSSP}-C_{minSSP})/C_{avgSSP}$] in plasma.

In another embodiment, the present application relates to a method of treating an inflammatory skin condition by administering a pharmaceutical composition comprising a therapeutically effective amount of minocycline to a subject in need thereof, wherein said composition upon oral administration for about 3 weeks or less exhibits a lower fluctuation index ($FI_{SSP}$) [$(C_{maxSSP}-C_{minSSP})/C_{avgSSP}$] in plasma.

In yet another embodiment, the present application relates to a method of treating rosacea by administering a pharmaceutical composition comprising a therapeutically effective amount of minocycline to a subject in need thereof, wherein said composition upon oral administration for about 3 weeks or less exhibits a lower fluctuation index ($FI_{SSP}$) [$(C_{maxSSP}-C_{minSSP})/C_{avgSSP}$] in plasma.

In yet another embodiment, the present application relates to a method of treating acne by administering a pharmaceutical composition comprising a therapeutically effective amount of minocycline to a subject in need thereof, wherein said composition upon oral administration for about 3 weeks or less exhibits a lower fluctuation index ($FI_{SSP}$) [$(C_{maxSSP}-C_{minSSP})/C_{avgSSP}$].

In another embodiment, the present application relates to a method of treating an inflammatory skin condition by administering a pharmaceutical composition comprising a therapeutically effective amount of minocycline to a subject in need thereof, wherein said composition upon oral administration for about 3 weeks or less exhibits a lower fluctuation index ($FI_{SSP}$) [$(C_{maxSSP}-C_{minSSP})/C_{avgSSP}$] in plasma, compared to an oral doxycycline composition comprising 40 mg of doxycycline.

In another embodiment, the present application relates to a method of treating rosacea by administering a pharmaceutical composition comprising a therapeutically effective amount of minocycline to a subject in need thereof, wherein said composition upon oral administration for about 3 weeks or less exhibits a lower fluctuation index ($FI_{SSP}$) [$(C_{maxSSP}-C_{minSSP})/C_{avgSSP}$] in plasma, compared to an oral doxycycline composition comprising 40 mg of doxycycline.

In another embodiment, the present application relates to a method of treating rosacea by administering a pharmaceutical composition comprising a therapeutically effective amount of minocycline to a subject in need thereof, wherein said composition upon oral administration for about 3 weeks or less exhibits at least about 30% lower fluctuation index ($FI_{SSP}$) [$(C_{maxSSP}-C_{minSSP})/C_{avgSSP}$] in plasma, compared to an oral doxycycline composition comprising 40 mg of doxycycline.

In an aspect of the above embodiments, the method of treating rosacea by administering a pharmaceutical composition comprising a therapeutically effective amount of minocycline to a subject in need thereof, wherein said administration for at least 3 weeks or less exhibits at least about 20%, about 15% or about 10% lower fluctuation index ($FI_{SSP}$) [$(C_{maxSSP}-C_{minSSP})/C_{avgSSP}$] in plasma, compared to an oral doxycycline composition comprising 40 mg of doxycycline.

In another aspect of the above embodiments, the present application relates to a method of treating an inflammatory skin condition by administering a pharmaceutical composition comprising a therapeutically effective amount of minocycline to a subject in need thereof, wherein said administration exhibits fluctuation index ($FI_{SSP}$) of about 0.9 to about 1.3.

In another aspect of the above embodiments, the present application relates to a method of treating rosacea by administering a pharmaceutical composition comprising a therapeutically effective amount of minocycline to a subject in need thereof, wherein said administration exhibits fluctuation index ($FI_{SSP}$) of about 0.9 to about 1.3.

In another aspect of the above embodiments, the present application relates to a method of treating acne by administering a pharmaceutical composition comprising a therapeutically effective amount of minocycline to a subject in need thereof, wherein said administration exhibits fluctuation index of about ($FI_{SSP}$) 0.9 to about 1.3.

In another aspect of the above embodiments, the present application relates to a method of treating an inflammatory skin condition by administering a pharmaceutical composition comprising a therapeutically effective amount of minocycline to a subject in need thereof, wherein said administration exhibits fluctuation index ($FI_{SSP}$) of about 1.0.

In another aspect of the above embodiments, the present application relates to a method of treating rosacea by administering a pharmaceutical composition comprising a therapeutically effective amount of minocycline to a subject in need thereof, wherein said administration exhibits fluctuation index ($FI_{SSP}$) of about 1.0.

In another aspect of the above embodiments, the present application relates to a method of treating acne by administering a pharmaceutical composition comprising a therapeutically effective amount of minocycline to a subject in need thereof, wherein said administration for about 3 weeks or less exhibits fluctuation index ($FI_{SSP}$) of about 1.0.

In another aspect of the above embodiments, the present application relates to a method of treating rosacea by administering a pharmaceutical composition comprising a therapeutically effective amount of minocycline to a subject in need thereof, wherein said administration for about 3 weeks or less exhibits lower variation in maximum plasma concentration ($C_{maxSSP}$) compared to an oral doxycycline composition comprising 40 mg of doxycycline.

In another aspect of the above embodiments, the present application relates to a method of treating rosacea by administering a pharmaceutical composition comprising a therapeutically effective amount of minocycline to a subject in need thereof, wherein said administration for about 3 weeks or less exhibits lower variation in minocycline exposure (AUC$_{0-tSSP}$) in plasma compared to an oral doxycycline composition comprising 40 mg of doxycycline.

In another aspect of the above embodiments, the present application relates to a method of treating rosacea by administering a pharmaceutical composition comprising a therapeutically effective amount of minocycline to a subject in need thereof, wherein said administration for about 3 weeks or less exhibits at least about 10% reduction in coefficient of variance (CV %) of maximum plasma concentration (C$_{maxSSP}$) compared to an oral doxycycline composition comprising 40 mg of doxycycline.

In another aspect of the above embodiments, the present application relates to a method of treating rosacea by administering a pharmaceutical composition comprising a therapeutically effective amount of minocycline to a subject in need thereof, wherein said administration for about 3 weeks or less exhibits at least about 10%, about 15% or about 20% reduction in coefficient of variance (CV %) of maximum plasma concentration (C$_{maxSSP}$) compared to an oral doxycycline composition comprising 40 mg of doxycycline.

In another aspect of the above embodiments, the present application relates to a method of treating rosacea by administering a pharmaceutical composition comprising a therapeutically effective amount of minocycline to a subject in need thereof, wherein said administration for about 3 weeks or less exhibits at least about 10% reduction in coefficient of variance (CV %) of minocycline exposure (AUC$_{0-tSSP}$) in plasma compared to an oral doxycycline composition comprising 40 mg of doxycycline.

In another aspect of the above embodiments, the present application relates to a method of treating rosacea by administering a pharmaceutical composition comprising a therapeutically effective amount of minocycline to a subject in need thereof, wherein said administration for about 3 weeks or less exhibits at least about 10%, about 15% or about 20% reduction in coefficient of variance (CV %) of minocycline exposure (AUC$_{0-tSSP}$) in plasma compared to an oral doxycycline composition comprising 40 mg of doxycycline.

In an embodiment, the present application relates to a method of treating an inflammatory skin condition by administering a pharmaceutical composition comprising a therapeutically effective amount of minocycline to a subject in need thereof, wherein said composition upon oral administration for about 3 weeks or less maintains steady state maximum plasma concentration (C$_{maxSSP}$) of minocycline.

In another embodiment, the present application relates to a method of treating an inflammatory skin condition by administering a pharmaceutical composition comprising a therapeutically effective amount of minocycline to a subject in need thereof, wherein said composition upon oral administration for about 3 weeks or less maintains steady state maximum interstitial fluid concentration (C$_{maxSSIF}$) of minocycline.

In another embodiment, the present application relates to a method of treating rosacea by administering a pharmaceutical composition comprising a therapeutically effective amount of minocycline to a subject in need thereof, wherein said composition upon oral administration for about 3 weeks or less maintains steady state maximum plasma concentration (C$_{maxSSP}$) of minocycline.

In another embodiment, the present application relates to a method of treating rosacea by administering a pharmaceutical composition comprising a therapeutically effective amount of minocycline to a subject in need thereof, wherein said composition upon oral administration for about 3 weeks or less maintains steady state maximum interstitial fluid concentration (C$_{maxSSIF}$) of minocycline.

In another embodiment, the present application relates to a method of treating acne by administering a pharmaceutical composition comprising a therapeutically effective amount of minocycline to a subject in need thereof, wherein said composition upon oral administration for about 3 weeks or less maintains steady state maximum plasma concentration (C$_{maxSSP}$) of minocycline.

In another embodiment, the present application relates to a method of treating acne by administering a pharmaceutical composition comprising a therapeutically effective amount of minocycline to a subject in need thereof, wherein said composition upon oral administration for about 3 weeks or less maintains steady state maximum interstitial fluid concentration (C$_{maxSSIF}$) of minocycline.

In yet another embodiment, the present application relates to a method of treating rosacea by administering a pharmaceutical composition comprising a therapeutically effective amount of minocycline to a subject in need thereof, wherein said composition upon oral administration for about 3 weeks or less exhibits plasma concentration ratio (C$_{maxSSP}$:C$_{maxP}$) of at least about 0.9 to about 1.3.

In an aspect of the above embodiments, the present application relates to a method of treating rosacea by administering a pharmaceutical composition comprising a therapeutically effective amount of minocycline to a subject in need thereof, wherein said administration exhibits plasma concentration ratio (C$_{maxSSP}$:C$_{maxP}$) of about 0.9.

In yet another embodiment, the present application relates to a method of treating rosacea by administering a pharmaceutical composition comprising a therapeutically effective amount of minocycline to a subject in need thereof, wherein said composition upon oral administration for about 3 weeks or less exhibits interstitial fluid concentration ratio (C$_{maxSSIF}$:C$_{maxIF}$) of at least about 0.7 to about 1.4.

In an aspect of the above embodiments, the present application relates to a method of treating rosacea by administering a pharmaceutical composition comprising a therapeutically effective amount of minocycline to a subject in need thereof, wherein said administration for about 3 weeks or less exhibits interstitial fluid concentration ratio (C$_{maxSSIF}$:C$_{maxIF}$) of about 1.0.

In an embodiment, the present application relates to a method of treating an inflammatory skin condition by administering a pharmaceutical composition comprising a therapeutically effective amount of minocycline to a subject in need thereof, wherein the said composition results in a desired steady state maximum plasma concentration (C$_{maxSSP}$) to treat said inflammatory skin condition.

In an embodiment, the present application relates to a method of treating an inflammatory skin condition by administering a pharmaceutical composition comprising a therapeutically effective amount of minocycline to a subject in need thereof, wherein the said composition results in a steady state maximum plasma concentration (C$_{maxSSP}$) of not more than about 500 ng/ml of minocycline.

In an embodiment, the present application relates to a method of treating an inflammatory skin condition by administering a pharmaceutical composition comprising a therapeutically effective amount of minocycline to a subject in need thereof, wherein the said composition results in a desired steady state maximum interstitial fluid concentration (C$_{maxSSIF}$) to treat the said inflammatory skin condition.

In another embodiment, the present application relates to a method of treating an inflammatory skin condition by administering a pharmaceutical composition comprising a therapeutically effective amount of minocycline to a subject in need thereof, wherein the said composition results in a steady state maximum interstitial fluid concentration ($C_{maxSSIF}$) of not more than about 200 ng/ml of minocycline.

In another embodiment, the present application relates to a method of treating rosacea by administering a pharmaceutical composition comprising a therapeutically effective amount of minocycline to a subject in need thereof, wherein said composition results in a steady state maximum plasma concentration ($C_{maxSSP}$) of not more than about 500 ng/ml of minocycline.

In another embodiment, the present application relates to a method of treating rosacea by administering a pharmaceutical composition comprising a therapeutically effective amount of minocycline to a subject in need thereof, wherein the said composition results in a steady state maximum plasma concentration ($C_{maxSSP}$) of not more than about 500 ng/ml, about 450 ng/ml, about 400 ng/ml, about 350 ng/ml or about 300 ng/ml of minocycline.

In another embodiment, the present application relates to a method of treating rosacea by administering a pharmaceutical composition comprising a therapeutically effective amount of minocycline to a subject in need thereof, wherein the said composition results in a steady state maximum interstitial fluid concentration ($C_{maxSSIF}$) of not more than about 200 ng/ml of minocycline.

In another embodiment, the present application relates to a method of treating rosacea by administering a pharmaceutical composition comprising a therapeutically effective amount of minocycline to a subject in need thereof, wherein the said composition results in a steady state maximum interstitial fluid concentration ($C_{maxSSIF}$) of not more than about 200 ng/ml, about 180 ng/ml, about 170 ng/ml, about 160 ng/ml or about 150 ng/ml of minocycline.

In an embodiment, the present application relates to a method of treating an inflammatory skin condition by administering a pharmaceutical composition comprising a therapeutically effective amount of minocycline to a subject in need thereof, wherein the said administration results in a desired maximum plasma concentration ($C_{maxP}$) on day 1 to treat the said inflammatory skin condition.

In one embodiment, the present application relates to a method of treating rosacea by administering a pharmaceutical composition comprising a therapeutically effective amount of minocycline to a subject in need thereof, wherein said administration results in a maximum plasma concentration ($C_{maxP}$) of not more than about 450 ng/ml of minocycline on day 1.

In another embodiment, the present application relates to a method of treating rosacea by administering a pharmaceutical composition comprising a therapeutically effective amount of minocycline to a subject in need thereof, wherein said administration results in a maximum plasma concentration ($C_{maxP}$) of not more than about 450 ng/ml, about 440 ng/ml or about 430 ng/ml of minocycline on day 1.

In an embodiment, the present application relates to a method of treating an inflammatory skin condition by administering a pharmaceutical composition comprising a therapeutically effective amount of minocycline to a subject in need thereof, wherein the said administration results in a desired maximum interstitial fluid concentration ($C_{maxIF}$) on day 1 to treat said inflammatory skin condition.

In another embodiment, the present application relates to a method of treating rosacea by administering a pharmaceutical composition comprising a therapeutically effective amount of minocycline to a subject in need thereof, wherein said administration results in a maximum interstitial fluid concentration ($C_{maxIF}$) of not more than about 150 ng/ml of minocycline on day 1.

In another embodiment, the present application relates to a method of treating rosacea by administering a pharmaceutical composition comprising a therapeutically effective amount of minocycline to a subject in need thereof, wherein said administration results in a maximum interstitial fluid concentration ($C_{maxIF}$) of not more than about 130 ng/ml, about 120 ng/ml or about 110 ng/ml of minocycline on day 1.

In an embodiment, the present application relates to a method of treating inflammatory skin condition by administering a pharmaceutical composition comprising a therapeutically effective amount of minocycline to a subject in need thereof, wherein the said administration for about 3 weeks or less maintains a desired plasma concentration of minocycline to treat said inflammatory skin condition.

In an embodiment, the present application relates to a method of treating rosacea by administering a pharmaceutical composition comprising a therapeutically effective amount of minocycline to a subject in need thereof, wherein said composition upon oral administration for about 3 weeks or less, maintains a desired plasma concentration of minocycline to treat said rosacea.

In an embodiment, the present application relates to a method of treating acne by administering a pharmaceutical composition comprising a therapeutically effective amount of minocycline to a subject in need thereof, wherein said composition upon oral administration for about 3 weeks or less, maintains a desired plasma concentration of minocycline to treat said acne.

In an aspect of the above embodiments, the method of treating rosacea by administering a pharmaceutical composition comprising a therapeutically effective amount of minocycline to a subject in need thereof, wherein said composition upon oral administration for about 3 weeks or less maintains a constant plasma concentration of not more than about 500 ng/ml to treat said rosacea.

In another aspect of the above embodiments, the method of treating rosacea by administering a pharmaceutical composition comprising a therapeutically effective amount of minocycline to a subject in need thereof, wherein said composition upon oral administration for about 3 weeks or less maintains a constant plasma concentration of not more than about 500 ng/ml to treat said rosacea.

In an embodiment, the present application relates to a method of treating rosacea by administering a pharmaceutical composition comprising a therapeutically effective amount of minocycline to a subject in need thereof, wherein said composition upon oral administration for about 3 weeks or less, maintains a desired interstitial fluid concentration of minocycline to treat said rosacea.

In another aspect of the above embodiments, the method of treating rosacea by administering a pharmaceutical composition comprising a therapeutically effective amount of minocycline to a subject in need thereof, wherein said composition upon oral administration for about 3 weeks or less, maintains a constant interstitial fluid concentration of not more than about 200 ng/ml of minocycline to treat said rosacea.

In another aspect of the above embodiments, the method of treating rosacea by administering a pharmaceutical composition comprising a therapeutically effective amount of minocycline to a subject in need thereof, wherein said composition upon oral administration for about 3 weeks or less, exhibits maximum interstitial fluid concentration ($C_{maxSSIF}$) of not more than about 200 ng/ml of minocycline to treat said rosacea.

In an embodiment, the present application relates to a method of treating rosacea by administering a pharmaceutical composition comprising a therapeutically effective amount of minocycline to a subject in need thereof, wherein said administration results in minocycline exposure in plasma ($AUC_{0-tP}$) of not more than about 4080 ng*hr/ml of minocycline on day 1.

In another embodiment, the present application relates to a method of treating rosacea by administering a pharmaceutical composition comprising a therapeutically effective amount of minocycline to a subject in need thereof, wherein said administration results in minocycline exposure in interstitial fluid ($AUC_{0-tIF}$) of not more than about 1625 ng*hr/ml of minocycline on day 1.

In another embodiment, the present application relates to a method of treating rosacea by administering a pharmaceutical composition comprising a therapeutically effective amount of minocycline to a subject in need thereof, wherein said administration results in minocycline exposure in plasma at steady state ($AUC_{0-tSSP}$) of not more than about 4550 ng*hr/ml of minocycline.

In another embodiment, the present application relates to a method of treating rosacea by administering a pharmaceutical composition comprising a therapeutically effective amount of minocycline to a subject in need thereof, wherein said administration results in minocycline exposure in interstitial fluid at steady state ($AUC_{0-tSSIF}$) of not more than about 1845 ng*hr/ml of minocycline.

In an embodiment, the present application relates to a method of treating rosacea by administering a pharmaceutical composition comprising a therapeutically effective amount of minocycline to a subject in need thereof, wherein said administration results in average plasma concentration ($C_{avgP}$) of not more than about 215 ng/ml of minocycline on day 1.

In another embodiment, the present application relates to a method of treating rosacea by administering a pharmaceutical composition comprising a therapeutically effective amount of minocycline to a subject in need thereof, wherein said administration results in average interstitial fluid concentration ($C_{avgIF}$) of not more than about 75 ng/ml of minocycline on day 1.

In an embodiment, the present application relates to a method of treating rosacea by administering a pharmaceutical composition comprising a therapeutically effective amount of minocycline to a subject in need thereof, wherein said administration results in average plasma concentration at steady state ($C_{avgSSP}$) of not more than about 245 ng/ml of minocycline.

In another embodiment, the present application relates to a method of treating rosacea by administering a pharmaceutical composition comprising a therapeutically effective amount of minocycline to a subject in need thereof, wherein said administration results in average interstitial fluid concentration at steady state ($C_{avgSSIF}$) of not more than about 90 ng/ml of minocycline.

In an embodiment, the present application relates to a method of treating rosacea by administering a pharmaceutical composition comprising about 20 mg of minocycline to a subject in need thereof, wherein said composition upon oral administration, exhibits ratio of minocycline exposure in interstitial fluid to plasma ($AUC_{0-tIF}/AUC_{0-tP}$) of at least about 10%, about 20%, about 30%, about 40% or about 50% higher as compared to oral administration of a doxycycline composition comprising 40 mg of doxycycline.

In an embodiment, the present application relates to a method of treating rosacea by administering a pharmaceutical composition comprising about 20 mg of minocycline to a subject in need thereof, wherein said composition upon oral administration for about 3 weeks or less, exhibits ratio of minocycline exposure in interstitial fluid to plasma ($AUC_{0-tSSIF}/AUC_{0-tSSP}$) of at least about 10%, about 20%, about 30%, about 40% or about 50% higher as compared to oral administration of a doxycycline composition comprising 40 mg of doxycycline.

In an aspect of the above embodiments, the method of treating rosacea by administering a pharmaceutical composition comprising about 20 mg of minocycline to a subject in need thereof, wherein said composition upon oral administration, exhibits ratio of minocycline exposure in interstitial fluid to plasma ($AUC_{0-tIF}/AUC_{0-tP}$) of at least about 35%, about 40%, about 45% or about 50%.

In an aspect of the above embodiments, the method of treating rosacea by administering a pharmaceutical composition comprising about 20 mg of minocycline to a subject in need thereof, wherein said composition upon oral administration for about 3 weeks or less, exhibits ratio of minocycline exposure in interstitial fluid to plasma ($AUC_{0-tSSIF}/AUC_{0-tSSP}$) of at least about 35%, about 40%, about 45% or about 50%.

In an embodiment, the present application relates to a method of treating rosacea by administering a pharmaceutical composition comprising about 30 mg of minocycline to a subject in need thereof, wherein said composition upon oral administration, exhibits ratio of minocycline exposure in interstitial fluid to plasma ($AUC_{0-tIF}/AUC_{0-tP}$) of at least about 10%, about 20%, about 30%, about 40% or about 50% higher as compared to oral administration of a doxycycline composition comprising 40 mg of doxycycline.

In an embodiment, the present application relates to a method of treating rosacea by administering a pharmaceutical composition comprising about 30 mg of minocycline to a subject in need thereof, wherein said composition upon oral administration for about 3 weeks or less, exhibits ratio of minocycline exposure in interstitial fluid to plasma ($AUC_{0-tSSIF}/AUC_{0-tSSP}$) of at least about 10%, about 20%, about 30%, about 40% or about 50% higher as compared to oral administration of a doxycycline composition comprising 40 mg of doxycycline.

In an aspect of the above embodiments, the method of treating rosacea by administering a pharmaceutical composition comprising about 30 mg of minocycline to a subject in need thereof, wherein said composition upon oral administration, exhibits ratio of minocycline exposure in interstitial fluid to plasma ($AUC_{0-tIF}/AUC_{0-tP}$) of at least about 35%, about 40%, about 45% or about 50%.

In an aspect of the above embodiments, the method of treating rosacea by administering a pharmaceutical composition comprising about 30 mg of minocycline to a subject in need thereof, wherein said composition upon oral administration for about 3 weeks or less, exhibits ratio of minocycline exposure in interstitial fluid to plasma ($AUC_{0-tSSIF}/AUC_{0-tSSP}$) of at least about 35%, about 40%, about 45% or about 50%.

In an embodiment, the present application relates to a method of treating rosacea by administering a pharmaceutical composition comprising about 40 mg of minocycline to a subject in need thereof, wherein said composition upon oral administration, exhibits ratio of minocycline exposure in interstitial fluid to plasma ($AUC_{0-tIF}/AUC_{0-tP}$) of at least about 10%, about 20%, about 30%, about 40% or about 50% higher as compared to oral administration of a doxycycline composition comprising 40 mg of doxycycline.

In an embodiment, the present application relates to a method of treating rosacea by administering a pharmaceutical composition comprising about 40 mg of minocycline to a subject in need thereof, wherein said composition upon oral administration for about 3 weeks or less, exhibits ratio of minocycline exposure in interstitial fluid to plasma ($AUC_{0-tSSIF}/AUC_{0-tSSP}$) of at least about 10%, about 20%, about 30%, about 40% or about 50% higher as compared to oral administration of a doxycycline composition comprising 40 mg of doxycycline.

In an aspect of the above embodiments, the method of treating rosacea by administering a pharmaceutical composition comprising about 40 mg of minocycline to a subject in need thereof, wherein said composition upon oral administration, exhibits ratio of minocycline exposure in interstitial fluid to plasma ($AUC_{0-tIF}/AUC_{0-tP}$) of at least about 35%, about 40%, about 45% or about 50%.

In an aspect of the above embodiments, the method of treating rosacea by administering a pharmaceutical composition comprising about 40 mg of minocycline to a subject in need thereof, wherein said composition upon oral administration for about 3 weeks or less, exhibits ratio of minocycline exposure in interstitial fluid to plasma ($AUC_{0-tSSIF}/AUC_{0-tSSP}$) of at least about 35%, about 40%, about 45% or about 50%.

In an embodiment, the present application relates to a method of treating rosacea by administering a pharmaceutical composition comprising about 20 mg of minocycline to a subject in need thereof, wherein said composition upon oral administration, exhibits ratio of average minocycline concentration in interstitial fluid to plasma or ($C_{avgIF}/C_{avgP}$) of at least about 10%, about 20%, about 30%, about 40% or about 50% higher as compared to oral administration of a doxycycline composition comprising 40 mg of doxycycline.

In an embodiment, the present application relates to a method of treating rosacea by administering a pharmaceutical composition comprising about 20 mg of minocycline to a subject in need thereof, wherein said composition upon oral administration for about 3 weeks or less, exhibits ratio of average minocycline concentration in interstitial fluid to plasma ($C_{avgSSIF}/C_{avgSSP}$) of at least about 10%, about 20%, about 30%, about 40% or about 50% higher as compared to oral administration of a doxycycline composition comprising 40 mg of doxycycline.

In an aspect of the above embodiments, the present application relates to a method of treating rosacea by administering a pharmaceutical composition comprising about 20 mg of minocycline to a subject in need thereof, wherein said composition upon oral administration, exhibits ratio of average minocycline concentration in interstitial fluid to plasma or ($C_{avgIF}/C_{avgP}$) of at least about 30%, about 35%, about 40% or about 45%.

In an aspect of the above embodiments, the present application relates to a method of treating rosacea by administering a pharmaceutical composition comprising about 20 mg of minocycline to a subject in need thereof, wherein said composition upon oral administration for about 3 weeks or less, exhibits ratio of average minocycline concentration in interstitial fluid to plasma or ($C_{avgSSIF}/C_{avgSSP}$) of at least about 30%, about 35%, about 40% or about 45%.

In an embodiment, the present application relates to a method of treating rosacea by administering a pharmaceutical composition comprising about 30 mg of minocycline to a subject in need thereof, wherein said composition upon oral administration, exhibits ratio of average minocycline concentration in interstitial fluid to plasma or ($C_{avgIF}/C_{avgP}$) of at least about 10%, about 20%, about 30%, about 40% or about 50% higher as compared to oral administration of a doxycycline composition comprising 40 mg of doxycycline.

In an embodiment, the present application relates to a method of treating rosacea by administering a pharmaceutical composition comprising about 30 mg of minocycline to a subject in need thereof, wherein said composition upon oral administration for about 3 weeks or less, exhibits ratio of average minocycline concentration in interstitial fluid to plasma ($C_{avgSSIF}/C_{avgSSP}$) of at least about 10%, about 20%, about 30%, about 40% or about 50% higher as compared to oral administration of a doxycycline composition comprising 40 mg of doxycycline.

In an aspect of the above embodiments, the present application relates to a method of treating rosacea by administering a pharmaceutical composition comprising about 30 mg of minocycline to a subject in need thereof, wherein said composition upon oral administration, exhibits ratio of average minocycline concentration in interstitial fluid to plasma or ($C_{avgIF}/C_{avgP}$) of at least about 30%, about 35%, about 40% or about 45%.

In an aspect of the above embodiments, the present application relates to a method of treating rosacea by administering a pharmaceutical composition comprising about 30 mg of minocycline to a subject in need thereof, wherein said composition upon oral administration for about 3 weeks or less, exhibits ratio of average minocycline concentration in interstitial fluid to plasma or ($C_{avgSSIF}/C_{avgSSP}$) of at least about 30%, about 35%, about 40% or about 45%.

In an embodiment, the present application relates to a method of treating rosacea by administering a pharmaceutical composition comprising about 40 mg of minocycline to a subject in need thereof, wherein said composition upon oral administration, exhibits ratio of average minocycline concentration in interstitial fluid to plasma or ($C_{avgIF}/C_{avgP}$) of at least about 10%, about 20%, about 30%, about 40% or about 50% higher as compared to oral administration of a doxycycline composition comprising 40 mg of doxycycline.

In an embodiment, the present application relates to a method of treating rosacea by administering a pharmaceutical composition comprising about 40 mg of minocycline to a subject in need thereof, wherein said composition upon oral administration for about 3 weeks or less, exhibits ratio of average minocycline concentration in interstitial fluid to plasma ($C_{avgSSIF}/C_{avgSSP}$) of at least about 10%, about 20%, about 30%, about 40% or about 50% higher as compared to oral administration of a doxycycline composition comprising 40 mg of doxycycline.

In an aspect of the above embodiments, the present application relates to a method of treating rosacea by administering a pharmaceutical composition comprising about 40 mg of minocycline to a subject in need thereof, wherein said composition upon oral administration, exhibits ratio of average minocycline concentration in interstitial fluid to plasma or ($C_{avgIF}/C_{avgP}$) of at least about 30%, about 35%, about 40% or about 45%.

In an aspect of the above embodiments, the present application relates to a method of treating rosacea by administering a pharmaceutical composition comprising about 40 mg of minocycline to a subject in need thereof, wherein said composition upon oral administration for about 3 weeks or less, exhibits ratio of average minocycline concentration in interstitial fluid to plasma or ($C_{avgSSIF}/C_{avgSSP}$) of at least about 30%, about 35%, about 40% or about 45%.

In an aspect of the above embodiments, the present application relates to a method of treating an inflammatory skin condition that comprises administering a pharmaceutical composition comprising a reduced dose of minocycline to a subject in need thereof, wherein said reduced dose comprises lower dose of minocycline compared to commercially available minocycline compositions, including 50 mg, 75 mg, or 100 mg minocycline compositions.

In an aspect of the above embodiments, the present application relates to a method of treating rosacea that comprises administering a pharmaceutical composition comprising a reduced dose of minocycline to a subject in need thereof, wherein said reduced dose comprises lower dose of minocycline compared to commercially available minocycline compositions, including 50 mg, 75 mg, or 100 mg minocycline compositions.

In an aspect of the above embodiments, the present application relates to a method of treating acne that comprises administering a pharmaceutical composition comprising a reduced dose of minocycline to a subject in need thereof, wherein said reduced dose comprises lower dose of minocycline compared to 50 mg, 75 mg or 100 mg minocycline compositions.

In an aspect of the above embodiments, the present application relates to a method of treating an inflammatory skin condition that comprises administering a pharmaceutical composition comprising a sub-antimicrobial dose of minocycline to a subject in need thereof.

In an aspect of the above embodiments, the present application relates to a method of treating rosacea that comprises administering a pharmaceutical composition comprising a sub-antimicrobial dose of minocycline to a subject in need thereof.

In an aspect of the above embodiments, the present application relates to a method of treating acne that comprises administering a pharmaceutical composition comprising a sub-antimicrobial dose of minocycline to a subject in need thereof.

In aspect of the above embodiments, the sub-antimicrobial dose of minocycline is less than 45 mg. In another aspect, the sub-antimicrobial dose is less than about 40 mg. In another aspect, the sub-antimicrobial dose is less than about 30 mg. In another aspect, the sub-antimicrobial dose is less than about 20 mg.

In another aspect of the above embodiments, the present application relates to a method of treating an inflammatory skin condition that comprises administering a pharmaceutical composition comprising a reduced dose of minocycline to a subject in need thereof, wherein said reduced dose comprises less than 45 mg dose of minocycline.

In another aspect of the above embodiments, the present application relates to a method of treating rosacea that comprises administering a pharmaceutical composition comprising a reduced dose of minocycline to a subject in need thereof, wherein said reduced dose comprises less than 45 mg dose of minocycline.

In another aspect of the above embodiments, the present application relates to a method of treating acne that comprises administering a pharmaceutical composition comprising a reduced dose of minocycline to a subject in need thereof, wherein said reduced dose comprises less than 45 mg dose of minocycline.

In another aspect of the above embodiments, the present application relates to a method of treating an inflammatory skin condition that comprises administering a pharmaceutical composition comprising a reduced dose of minocycline to a subject in need thereof. In an embodiment, the reduced dose comprises less than 45 mg of minocycline.

In another aspect of the above embodiments, the present application relates to a method of treating an inflammatory skin condition comprises administering a pharmaceutical composition comprising a reduced dose of minocycline to a subject in need thereof, wherein said reduced dose comprises about 40 mg; about 35 mg; about 30 mg; about 25 mg; about 20 mg; about 15 mg; or about 10 mg of minocycline.

In another aspect of the above embodiments, the present application relates to a method of treating rosacea that comprises administering a pharmaceutical composition comprising a reduced dose of minocycline to a subject in need thereof. In an embodiment, the reduced dose comprises less than 45 mg, less than 40 mg, less than 35 mg, less than 30 mg, less than 25 mg, less than 20 mg, less than 15 mg, or less than 10 mg. In an embodiment, the reduced dose comprises about 40 mg, about 35 mg, about 30 mg, about 25 mg, about 20 mg, about 15 mg, or about 10 mg of minocycline.

In another aspect of the above embodiments, the present application relates to a method of treating acne that comprises administering a pharmaceutical composition comprising a reduced dose of minocycline to a subject in need thereof. In an embodiment, the reduced dose comprises less than 45 mg, less than 40 mg, less than 35 mg, less than 30 mg, less than 25 mg, less than 20 mg, less than 15 mg, or less than 10 mg. In an embodiment, the reduced dose comprises about 40 mg, about 35 mg, about 30 mg, about 25 mg, about 20 mg, about 15 mg, or about 10 mg of minocycline.

In another aspect of the above embodiments, the present application relates to a method of treating rosacea that comprises administering a pharmaceutical composition comprising a reduced dose of minocycline to a subject in need thereof, wherein said reduced dose comprises about 10 mg to about 40 mg of minocycline.

In another aspect of the above embodiments, the present application relates to a method of treating rosacea that comprises administering a pharmaceutical composition comprising a reduced dose of minocycline to a subject in need thereof, wherein said reduced dose comprises about 20 mg to about 40 mg of minocycline.

In another aspect of the above embodiments, the present application relates to a method of treating rosacea that comprises administering a pharmaceutical composition comprising a reduced dose of minocycline to a subject in need thereof, wherein said reduced dose comprises about 20 mg of minocycline.

In another aspect of the above embodiments, the present application relates to a method of treating rosacea that comprises administering a pharmaceutical composition comprising a reduced dose of minocycline to a subject in need thereof, wherein said reduced dose comprises about 30 mg of minocycline.

In another aspect of the above embodiments, the present application relates to a method of treating rosacea that comprises administering a pharmaceutical composition comprising a reduced dose of minocycline to a subject in need thereof, wherein said reduced dose comprises about 40 mg of minocycline.

In an aspect of the above embodiments, the present application relates to a method of treating rosacea by administering an oral pharmaceutical composition comprising about 20 mg of minocycline to a subject in need thereof, wherein said administration results in an equivalent efficacy as compared to an oral doxycycline composition comprising 40 mg of doxycycline.

In another aspect of the above embodiments, the present application relates to a method of treating rosacea by administering an oral pharmaceutical composition comprising about 40 mg of minocycline to a subject in need thereof, wherein said administration results in improved efficacy as compared to an oral doxycycline composition comprising 40 mg of doxycycline.

In an aspect of the above embodiments, the present application relates to a method of treating rosacea in a subject in need thereof, comprising selecting the subject for whom treatment with an oral doxycycline composition comprising 40 mg of doxycycline is ineffective or effective, and administering an oral pharmaceutical composition comprising less than 45 mg of minocycline.

In an aspect of the above embodiments, the present application relates to a method of treating rosacea in a subject in need thereof, comprising selecting the subject for whom treatment with an oral doxycycline composition comprising 40 mg of doxycycline is ineffective or effective, and administering an oral pharmaceutical composition comprising about 10 mg or about 40 mg of minocycline.

In another aspect of the above embodiments, the present application relates to a method of treating rosacea in a subject in need thereof, comprising selecting the subject for whom treatment with an oral doxycycline composition comprising 40 mg of doxycycline is ineffective or effective, and administering an oral pharmaceutical composition comprising about 20 mg of minocycline.

In another aspect of the above embodiments, the present application relates to a method of treating rosacea in a subject in need thereof, comprising selecting the subject for whom treatment with an oral doxycycline composition comprising 40 mg of doxycycline is ineffective or effective, and administering an oral pharmaceutical composition comprising about 30 mg of minocycline.

In another aspect of the above embodiments, the present application relates to a method of treating rosacea in a subject in need thereof, comprising selecting the subject for whom treatment with an oral doxycycline composition comprising 40 mg of doxycycline is ineffective or effective, and administering an oral pharmaceutical composition comprising about 40 mg of minocycline.

In an aspect of the above embodiments, the present application relates to a method of treating rosacea in a subject in need thereof, comprising selecting the subject for whom treatment with an oral doxycycline composition comprising 40 mg of doxycycline is ineffective or effective, and administering an oral pharmaceutical composition comprising less than 45 mg of minocycline.

In an aspect of the above embodiments, the present application relates to a method of treating rosacea in a subject in need thereof, comprising selecting the subject for whom treatment with an oral doxycycline composition comprising 40 mg of doxycycline is effective, and administering an oral pharmaceutical composition comprising about 10 mg or about 40 mg of minocycline.

In another aspect of the above embodiments, the present application relates to a method of treating rosacea in a subject in need thereof, comprising selecting the subject for whom treatment with an oral doxycycline composition comprising 40 mg of doxycycline is effective, and administering an oral pharmaceutical composition comprising about 20 mg of minocycline.

In another aspect of the above embodiments, the present application relates to a method of treating rosacea in a subject in need thereof, comprising selecting the subject for whom treatment with an oral doxycycline composition comprising 40 mg of doxycycline is effective, and administering an oral pharmaceutical composition comprising about 30 mg of minocycline.

In another aspect of the above embodiments, the present application relates to a method of treating rosacea in a subject in need thereof, comprising selecting the subject for whom treatment with an oral doxycycline composition comprising 40 mg of doxycycline is effective, and administering an oral pharmaceutical composition comprising less than about 40 mg of minocycline.

In yet another aspect of the above embodiments, the present application relates to a method of treating rosacea in a subject in need thereof, comprising:
  (a) selecting the subject for whom treatment with an oral doxycycline composition comprising 40 mg of doxycycline is ineffective, and administering an oral pharmaceutical composition comprising about 20 mg, about 30 mg, or about 40 mg of minocycline; or
  (b) selecting the subject for whom treatment with an oral doxycycline composition comprising 40 mg of doxycycline is effective, and administering an oral pharmaceutical composition comprising about 20 mg, about 30 mg, or less than about 40 mg of minocycline.

In yet another aspect of the above embodiments, the present application relates to a method of treating rosacea in a subject in need thereof, comprising:
  (c) selecting the subject for whom treatment with an oral doxycycline composition comprising 40 mg of doxycycline is ineffective, and administering an oral pharmaceutical composition comprising about 20 mg, about 30 mg, or about 40 mg of minocycline; or
  (d) selecting the subject for whom treatment with an oral doxycycline composition comprising 40 mg of doxycycline is effective, and administering an oral pharmaceutical composition comprising about 20 mg, about 30 mg, or about 40 mg of minocycline.

In an aspect of the above embodiments, the present application relates to a method of treating an inflammatory skin condition by administering a pharmaceutical composition comprising a reduced dose of minocycline to a subject in need thereof, wherein said reduced dose provides desired plasma concentration of minocycline for treating the inflammatory skin condition.

In an aspect of the above embodiments, the present application relates to a method of treating inflammatory lesions by administering a pharmaceutical composition comprising a reduced dose of minocycline to a subject in need thereof, wherein said reduced dose provides desired interstitial fluid concentration of minocycline for treating said inflammatory lesions.

In another aspect of the above embodiments, the present application relates to a method of treating rosacea by administering a pharmaceutical composition comprising a reduced dose of minocycline to a subject in need thereof, wherein said reduced dose provides desired plasma concentration of minocycline for treating said rosacea.

In another aspect of the above embodiments, the present application relates to a method of treating rosacea by administering a pharmaceutical composition comprising a reduced dose of minocycline to a subject in need thereof, wherein said reduced dose provides desired interstitial fluid concentration of minocycline for treating said rosacea.

In another aspect of the above embodiments, the present application relates to a method of treating acne by administering a pharmaceutical composition comprising a reduced dose of minocycline to a subject in need thereof, wherein said reduced dose provides desired plasma concentration of minocycline for treating said acne.

In another aspect of the above embodiments, the present application relates to a method of treating acne by administering a pharmaceutical composition comprising a reduced dose of minocycline to a subject in need thereof, wherein said reduced dose provides sufficient interstitial fluid concentration of minocycline for treating said acne.

In another aspect of the above embodiments, the present application relates to a method of treating rosacea by administering a pharmaceutical composition comprising a reduced dose of minocycline to a subject in need thereof, wherein said reduced dose comprises less than 45 mg dose of minocycline to provide a steady state maximum plasma concentration of not more than about 500 ng/ml of minocycline for treating said rosacea.

In another aspect of the above embodiments, the present application relates to a method of treating rosacea by administering a pharmaceutical composition comprising a reduced dose of minocycline to a subject in need thereof, wherein said reduced dose comprises less than 45 mg dose of minocycline to provide a steady state maximum interstitial fluid concentration of not more than about 200 ng/ml of minocycline for treating said rosacea.

In an aspect of the above embodiments, the present application relates to a method of treating rosacea comprises administering a pharmaceutical composition comprising about 10 mg to about 40 mg of minocycline to a subject in need thereof, wherein said administration to the subjects results in at least one of the following pharmacokinetic parameters when measured in plasma samples on day 1:
(a) $C_{maxP}$ of about 55 ng/ml to about 450 ng/ml;
(b) $AUC_{0-tP}$ of about 830 ng*hr/ml to about 4080 ng*hr/ml; or
(c) $C_{avgP}$ of about 30 ng/ml to about 215 ng/ml.

In another aspect of the above embodiments, the present application relates to a method of treating rosacea comprises administering a pharmaceutical composition comprising about 10 mg to about 40 mg of minocycline to a subject in need thereof, wherein said administration to the subjects results in at least one of the following pharmacokinetic parameters when measured in interstitial fluid samples on day 1:
(a) $C_{maxIF}$ of about 14 ng/ml to about 150 ng/ml;
(b) $AUC_{0-tIF}$ of about 250 ng*hr/ml to about 1625 ng*hr/ml; or
(c) $C_{avgIF}$ of about 5 ng/ml to about 75 ng/ml.

In another aspect of the above embodiments, the present application relates to a method of treating rosacea comprises administering a pharmaceutical composition comprising about 10 mg to about 40 mg of minocycline to a subject in need thereof, wherein said administration to the subjects results in at least one of the following steady state pharmacokinetic parameters when measured in plasma samples:
(a) $C_{maxSSP}$ of about 70 ng/ml to about 440 ng/ml;
(b) $AUC_{0-tSSP}$ of about 830 ng*hr/ml to about 4550 ng*hr/ml; or
(c) $C_{avgSSP}$ of about 40 ng/ml to about 245 ng/ml.

In another aspect of the above embodiments, the present application relates to a method of treating rosacea comprises administering a pharmaceutical composition comprising about 10 mg to about 40 mg of minocycline to a subject in need thereof, wherein said administration to the subjects results in at least one of the following steady state pharmacokinetic parameters when measured in interstitial fluid samples:
(a) $C_{maxSSIF}$ of about 15 ng/ml to about 150 ng/ml;
(b) $AUC_{0-tSSIF}$ of about 375 ng*hr/ml to about 1845 ng*hr/ml; or
(c) $C_{avgSSIF}$ of about 8 ng/ml to about 90 ng/ml.

In another embodiment, the present application relates to a method of treating rosacea by administering a pharmaceutical composition comprising about 20 mg of minocycline to a subject in need thereof, wherein said administration results in at least one of the following pharmacokinetic parameters when measured in plasma samples on day 1:
(a) $C_{maxP}$ of about 110 ng/ml to about 150 ng/ml;
(b) $AUC_{0-tP}$ of about 1210 ng*hr/ml to about 1625 ng*hr/ml; or
(c) $C_{avgP}$ of about 60 ng/ml to about 85 ng/ml.

In another embodiment, the present application relates to a method of treating rosacea by administering a pharmaceutical composition comprising about 20 mg of minocycline to a subject in need thereof, wherein said administration results in at least one of the following pharmacokinetic parameters when measured in interstitial fluid samples on day 1:
(a) $C_{maxIF}$ of about 37 ng/ml to about 60 ng/ml;
(b) $AUC_{0-tIF}$ of about 500 ng*hr/ml to about 680 ng*hr/ml; or
(c) $C_{avgIF}$ of about 22 ng/ml to about 30 ng/ml.

In another embodiment, the present application relates to a method of treating rosacea by administering a pharmaceutical composition comprising about 20 mg of minocycline to a subject in need thereof, wherein said administration results in at least one of the following steady state pharmacokinetic parameters when measured in plasma samples:
(a) $C_{maxSSP}$ of about 140 ng/ml to about 190 ng/ml;
(b) $AUC_{0-tSSP}$ of about 1660 ng*hr/ml to about 2245 ng*hr/ml; or
(c) $C_{avgSSP}$ of about 80 ng/ml to about 110 ng/ml.

In another embodiment, the present application relates to a method of treating rosacea by administering a pharmaceutical composition comprising about 20 mg of minocycline to a subject in need thereof, wherein said administration results in at least one of the following steady state pharmacokinetic parameters when measured in interstitial fluid samples:
(a) $C_{maxSSIF}$ of about 52 ng/ml to about 70 ng/ml;
(b) $AUC_{0-tSSIF}$ of about 745 ng*hr/ml to about 1010 ng*hr/ml; or
(c) $C_{avgSSIF}$ of about 32 ng/ml to about 43 ng/ml.

In another embodiment, the present application relates to a method of treating rosacea by administering a pharmaceutical composition comprising about 30 mg of minocycline to a subject in need thereof, wherein said administration results in at least one of the following pharmacokinetic parameters when measured in plasma samples on day 1:
(a) $C_{maxP}$ of about 224 ng/ml to about 330 ng/ml;
(b) $AUC_{0-tP}$ of about 2215 ng*hr/ml to about 3107 ng*hr/ml; or
(c) $C_{avgP}$ of about 90 ng/ml to about 120 ng/ml.

In another embodiment, the present application relates to a method of treating rosacea by administering a pharmaceutical composition comprising about 30 mg of minocycline to a subject in need thereof, wherein said administration results in at least one of the following pharmacokinetic parameters when measured in interstitial fluid samples on day 1:
(a) $C_{maxIF}$ of about 70 ng/ml to about 95 ng/ml;
(b) $AUC_{0-tIF}$ of about 900 ng*hr/ml to about 1215 ng*hr/ml; or
(c) $C_{avgIF}$ of about 40 ng/ml to about 50 ng/ml.

In another embodiment, the present application relates to a method of treating rosacea by administering a pharmaceutical composition comprising about 30 mg of minocycline to a subject in need thereof, wherein said administration results in at least one of the following steady state pharmacokinetic parameters when measured in plasma samples:
(a) $C_{maxSSP}$ of about 215 ng/ml to about 290 ng/ml;
(b) $AUC_{0-tSSP}$ of about 2525 ng*hr/ml to about 3415 ng*hr/ml; or
(c) $C_{avgSSP}$ of about 140 ng/ml to about 180 ng/ml.

In another embodiment, the present application relates to a method of treating rosacea by administering a pharmaceutical composition comprising about 30 mg of minocycline to a subject in need thereof, wherein said administration results in at least one of the following steady state pharmacokinetic parameters when measured in interstitial fluid samples:
(a) $C_{maxSSIF}$ of about 80 ng/ml to about 110 ng/ml;
(b) $AUC_{0-tSSIF}$ of about 1025 ng*hr/ml to about 1385 ng*hr/ml; or
(c) $C_{avgSSIF}$ of about 50 ng/ml to about 65 ng/ml.

In another embodiment, the present application relates to a method of treating rosacea by administering a pharmaceutical composition comprising about 40 mg of minocycline to a subject in need thereof, wherein said administration results in at least one of the following pharmacokinetic parameters when measured in plasma samples on day 1:
(a) $C_{maxP}$ of about 325 ng/ml to about 440 ng/ml;
(b) $AUC_{0-tP}$ of about 3115 ng*hr/ml to about 4080 ng*hr/ml; or
(c) $C_{avgP}$ of about 160 ng/ml to about 215 ng/ml.

In another embodiment, the present application relates to a method of treating rosacea by administering a pharmaceutical composition comprising about 40 mg of minocycline to a subject in need thereof, wherein said administration results in at least one of the following pharmacokinetic parameters when measured in interstitial fluid samples on day 1:
(a) $C_{maxIF}$ of about 95 ng/ml to about 150 ng/ml;
(b) $AUC_{0-tIF}$ of about 1200 ng*hr/ml to about 1625 ng*hr/ml; or
(c) $C_{avgIF}$ of about 55 ng/ml to about 75 ng/ml.

In another embodiment, the present application relates to a method of treating rosacea by administering a pharmaceutical composition comprising about 40 mg of minocycline to a subject in need thereof, wherein said administration results in at least one of the following steady state pharmacokinetic parameters when measured in plasma samples:
(a) $C_{maxSSP}$ of about 285 ng/ml to about 410 ng/ml;
(b) $AUC_{0-tSSP}$ of about 3365 ng*hr/ml to about 4550 ng*hr/ml; or
(c) $C_{avgSSP}$ of about 175 ng/ml to about 245 ng/ml.

In another embodiment, the present application relates to a method of treating rosacea by administering a pharmaceutical composition comprising about 40 mg of minocycline to a subject in need thereof, wherein said administration results in at least one of the following steady state pharmacokinetic parameters when measured in interstitial fluid samples:
(a) $C_{maxSSIF}$ of about 105 ng/ml to about 145 ng/ml;
(b) $AUC_{0-tSSIF}$ of about 1365 ng*hr/ml to about 1845 ng*hr/ml; or
(c) $C_{avgSSIF}$ of about 65 ng/ml to about 90 ng/ml.

In an aspect of the above embodiments, the present application relates to a method of treating rosacea by administering a pharmaceutical composition comprising about 40 mg of minocycline to a subject in need thereof, wherein said administration for about 3 weeks or less, exhibits plasma concentration ratio ($C_{maxSSP}$:$C_{maxP}$) of at least about 30% lower ratio compared to an oral doxycycline composition comprising 40 mg of doxycycline.

In another aspect of the above embodiments, the present application relates to a method of treating rosacea by administering a pharmaceutical composition comprising about 40 mg of minocycline to a subject in need thereof, wherein said administration for about 3 weeks or less, exhibits plasma concentration ratio ($C_{maxSSP}$:$C_{maxP}$) of at least about 30%, about 35%, about 40%, about 45% or about 50% lower ratio compared to an oral doxycycline composition comprising 40 mg of doxycycline.

In another aspect of the above embodiments, the present application relates to a method of treating rosacea by administering a pharmaceutical composition comprising about 40 mg of minocycline to a subject in need thereof, wherein said administration for about 3 weeks or less, exhibits average plasma concentration ($C_{avgSSP}$) of at least about 20% lower compared to an oral doxycycline composition comprising 40 mg of doxycycline.

In another aspect of the above embodiments, the present application relates to a method of treating rosacea by administering a pharmaceutical composition comprising about 40 mg of minocycline to a subject in need thereof, wherein said administration for about 3 weeks or less, exhibits average plasma concentration ($C_{avgSSP}$) of at least about 20%, about 25%, about 30%, about 35% or about 40% lower compared to an oral doxycycline composition comprising 40 mg of doxycycline.

In an embodiment, the present application relates to a method of treating rosacea by administering a pharmaceutical composition comprising about 10 mg to about 40 mg of minocycline, to a subject in need thereof, upon oral administration exhibits at least one of the following pharmacokinetic parameters, when measured in plasma samples:
(a) $C_{max}/D$ of about 5 ng/ml/mg to about 11 ng/ml/mg; or
(b) $AUC_{0-t}/D$ of about 60 ng/ml/mg to about 102 ng/ml/mg.

In another embodiment, the present application relates to a method of treating rosacea by administering a pharmaceutical composition comprising about 10 mg to about 40 mg of minocycline, to a subject in need thereof, upon oral administration for about 3 weeks or less exhibits at least one of the following pharmacokinetic parameters, when measured in plasma samples:
(a) $C_{maxSSP}/D$ of about 5 ng/ml/mg to about 12 ng/ml/mg; or
(b) $AUC_{0-tSSP}/D$ of about 60 ng/ml/mg to about 114 ng/ml/mg.

In an aspect of the above embodiments, the present application relates to a method of treating rosacea by administering a pharmaceutical composition comprising about 20 mg of minocycline, to a subject in need thereof, upon oral administration exhibits at least one of the following pharmacokinetic parameters, when measured in plasma samples:
(a) $C_{maxP}/D$ of about 5.5 ng/ml/mg to about 7.5 ng/ml/mg; or
(b) $AUC_{0-tP}/D$ of about 60 ng/ml/mg to about 80 ng/ml/mg.

In another aspect of the above embodiments, the present application relates to a method of treating rosacea by administering a pharmaceutical composition comprising about 20 mg of minocycline, to a subject in need thereof, upon oral administration for about 3 weeks or less exhibits at least one of the following pharmacokinetic parameters, when measured in plasma samples:
(a) $C_{maxSSP}/D$ of about 7 ng/ml/mg to about 9.5 ng/ml/mg; or
(b) $AUC_{0-tSSP}/D$ of about 80 ng/ml/mg to about 112 ng/ml/mg.

In an aspect of the above embodiments, the present application relates to a method of treating rosacea by administering a pharmaceutical composition comprising about 30 mg of minocycline, to a subject in need thereof, upon oral administration exhibits at least one of the following pharmacokinetic parameters, when measured in plasma samples:

(c) $C_{maxP}/D$ of about 8.3 ng/ml/mg to about 10.8 ng/ml/mg; or (d) $AUC_{0\text{-}tP}/D$ of about 75 ng/ml/mg to about 100 ng/ml/mg.

In another aspect of the above embodiments, the present application relates to a method of treating rosacea by administering a pharmaceutical composition comprising about 30 mg of minocycline, to a subject in need thereof, upon oral administration for about 3 weeks or less exhibits at least one of the following pharmacokinetic parameters, when measured in plasma samples:

(c) $C_{maxSSP}/D$ of about 7 ng/ml/mg to about 9.5 ng/ml/mg; or (d) $AUC_{0\text{-}tSSP}/D$ of about 85 ng/ml/mg to about 112 ng/ml/mg.

In another aspect of the above embodiments, the present application relates to a method of treating rosacea by administering a pharmaceutical composition comprising about 40 mg of minocycline, to a subject in need thereof, upon oral administration exhibits at least one of the following pharmacokinetic parameters, when measured in plasma samples:

(a) $C_{maxP}/D$ of about 8 ng/ml/mg to about 11 ng/ml/mg; or (b) $AUC_{0\text{-}tP}/D$ of about 75 ng/ml/mg to about 102 ng/ml/mg.

In another aspect of the above embodiments, the present application relates to a method of treating rosacea by administering a pharmaceutical composition comprising about 40 mg of minocycline, to a subject in need thereof, upon oral administration for about 3 weeks or less exhibits at least one of the following pharmacokinetic parameters, when measured in plasma samples:

(a) $C_{maxSSP}/D$ of about 7.2 ng/ml/mg to about 9.6 ng/ml/mg; or (b) $AUC_{0\text{-}tSSP}/D$ of about 84 ng/ml/mg to about 114 ng/ml/mg.

In an embodiment, the present application relates to a method of treating rosacea by administering a pharmaceutical composition comprising about 10 mg to about 40 mg dose of minocycline, to a subject in need thereof, upon oral administration exhibits at least one of the following pharmacokinetic parameters, when measured in interstitial fluid samples:

(a) $C_{maxIF}/D$ of about 1.8 ng/ml/mg to about 3 ng/ml/mg; or (b) $AUC_{0\text{-}tIF}/D$ of about 25 ng/ml/mg to about 40 ng/ml/mg.

In another embodiment, the present application relates to a method of treating rosacea by administering a pharmaceutical composition comprising about 10 mg to about 40 mg dose of minocycline, to a subject in need thereof, upon oral administration for about 3 weeks or less exhibits at least one of the following pharmacokinetic parameters, when measured in interstitial fluid samples:

(a) $C_{maxSSIF}/D$ of about 1.3 ng/ml/mg to about 3.6 ng/ml/mg; or (b) $AUC_{0\text{-}tSSIF}/D$ of about 34 ng/ml/mg to about 46 ng/ml/mg.

In an aspect of the above embodiments, the present application relates to a method of treating rosacea by administering a pharmaceutical composition comprising about 20 mg of minocycline, to a subject in need thereof, upon oral administration exhibits at least one of the following pharmacokinetic parameters, when measured in interstitial fluid samples:

(a) $C_{maxIF}/D$ of about 1.8 ng/ml/mg to about 2.4 ng/ml/mg; or (b) $AUC_{0\text{-}tIF}/D$ of about 25 ng/ml/mg to about 34 ng/ml/mg.

In another aspect of the above embodiments, the present application relates to a method of treating rosacea by administering a pharmaceutical composition comprising about 20 mg of minocycline, to a subject in need thereof, upon oral administration for about 3 weeks or less exhibits at least one of the following pharmacokinetic parameters, when measured in interstitial fluid samples:

(a) $C_{maxSSIF}/D$ of about 2.6 ng/ml/mg to about 3.5 ng/ml/mg; or (b) $AUC_{0\text{-}tSSIF}/D$ of about 37 ng/ml/mg to about 50 ng/ml/mg.

In an aspect of the above embodiments, the present application relates to a method of treating rosacea by administering a pharmaceutical composition comprising about 30 mg of minocycline, to a subject in need thereof, upon oral administration exhibits at least one of the following pharmacokinetic parameters, when measured in interstitial fluid samples:

(c) $C_{maxIF}/D$ of about 2.3 ng/ml/mg to about 3.0 ng/ml/mg; or (d) $AUC_{0\text{-}tIF}/D$ of about 30 ng/ml/mg to about 40 ng/ml/mg.

In another aspect of the above embodiments, the present application relates to a method of treating rosacea by administering a pharmaceutical composition comprising about 30 mg of minocycline, to a subject in need thereof, upon oral administration for about 3 weeks or less exhibits at least one of the following pharmacokinetic parameters, when measured in interstitial fluid samples:

(c) $C_{maxSSIF}/D$ of about 2.6 ng/ml/mg to about 3.5 ng/ml/mg; or (d) $AUC_{0\text{-}tSSIF}/D$ of about 36 ng/ml/mg to about 44 ng/ml/mg.

In another aspect of the above embodiments, the present application relates to a method of treating rosacea by administering a pharmaceutical composition comprising about 40 mg of minocycline, to a subject in need thereof, upon oral administration exhibits at least one of the following pharmacokinetic parameters, when measured in interstitial fluid samples:

(a) $C_{maxIF}/D$ of about 2.3 ng/ml/mg to about 3.1 ng/ml/mg; or (b) $AUC_{0\text{-}tIF}/D$ of about 30 ng/ml/mg to about 40 ng/ml/mg.

In another aspect of the above embodiments, the present application relates to a method of treating rosacea by administering a pharmaceutical composition comprising about 40 mg of minocycline, to a subject in need thereof, upon oral administration for about 3 weeks or less exhibits at least one of the following pharmacokinetic parameters, when measured in interstitial fluid samples:

(a) $C_{maxSSIF}/D$ of about 2.6 ng/ml/mg to about 3.6 ng/ml/mg; or (b) $AUC_{0\text{-}tSSIF}/D$ of about 34 ng/ml/mg to about 46 ng/ml/mg.

In an aspect of the above embodiments, the present application relates to a method of treating an inflammatory skin condition or inflammatory lesions resulting from one or more of rosacea, acne, atopic dermatitis, folliculitis, perioral dermatitis, photo-damage, actinic keratosis, psoriasis, treatment of chronic wounds, bed sores, keratosis pilaris, scars including surgical and acne scars, sebaceous cysts, inflammatory dermatoses, post inflammatory hyperpigmentation, xerosis, pruritis, lichen planus, nodular prurigo, eczema, or miliaria.

In an aspect of the above embodiments, the method of treating rosacea by administering an oral pharmaceutical composition comprising a reduced dose of minocycline to a subject in need thereof, wherein said rosacea is a papulopustular rosacea, acne rosacea, an erythematotelangiectatic rosacea, a phymatous rosacea, an ocular rosacea, an acne rosacea, a pyoderma faciale, a rosacea conglobate, a mild rosacea, a moderate rosacea, a severe rosacea, a mild to moderate rosacea, or a moderate to severe rosacea.

In an aspect of the above embodiments, the method of treating acne by administering an oral pharmaceutical composition comprising a reduced dose of minocycline to a subject in need thereof, wherein said acne is acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstrual acne, acne pustulosa, acne scorbutica, acne scrofulosorum, acne urticata, acne varioliformis, acne venenata, propionic acne, acne excoriee, gram negative acne, steroid acne, and nodulocystic acne.

In another aspect of the above embodiments, the method of treating rosacea by administering an oral pharmaceutical composition comprising a reduced dose of minocycline to a subject in need thereof, wherein said rosacea is characterized by inflammatory lesions.

In another aspect of the above embodiments, the method of treating rosacea by administering an oral pharmaceutical composition comprising a reduced dose of minocycline to a subject in need thereof, wherein said rosacea is characterized by papules, pustules and/or nodules.

In an aspect of the above embodiments, the present application relates to a method of treating an inflammatory skin condition by administering a pharmaceutical composition comprising a therapeutic effective amount of less than 45 mg dose of minocycline to a subject in need thereof, wherein the inflammatory skin condition include rosacea.

In an aspect of the above embodiments, the present application relates to a method of treating an inflammatory skin condition by administering a pharmaceutical composition comprising a therapeutic effective amount of less than 45 mg dose of minocycline to a subject in need thereof, wherein the inflammatory skin condition is selected from the group consisting of a papulopustular rosacea an erythematotelangiectatic rosacea, a phymatous rosacea or an ocular rosacea, an acne rosacea, a pyoderma faciale, a rosacea conglobate, a mild rosacea, a moderate rosacea, a severe rosacea, a mild to moderate rosacea, and a moderate to severe rosacea.

In an aspect of the above embodiments, the present application relates to a method of treating an inflammatory skin condition by administering a pharmaceutical composition comprising a therapeutic effective amount of less than 45 mg dose of minocycline to a subject in need thereof, wherein the inflammatory skin condition includes acne.

In an aspect of the above embodiments, the method of treating rosacea by administering a reduced dose of minocycline, wherein said administration significantly reduced the severity of rosacea as compared to the severity of rosacea before the treatment.

In an aspect of the above embodiments, the method of treating rosacea by administering a reduced dose of minocycline, wherein said administration significantly reduced the severity of rosacea as compared to the severity of rosacea before the treatment, and wherein said severity of the rosacea is assessed using IGA scale.

In an aspect of the above embodiments, the method of treating rosacea by administering a reduced dose of minocycline, wherein said administration significantly reduces the IGA score compared to the IGA score before the treatment.

In an aspect of the above embodiments, the method of treating rosacea by administering a reduced dose of minocycline, wherein said administration significantly reduces the IGA score compared to the IGA score of placebo composition.

In an aspect of the above embodiments, the method of treating rosacea by administering a reduced dose of minocycline, wherein said administration reduces the IGA score of the subject by at least one grade compared to the IGA score before the treatment.

In an aspect of the above embodiments, the method of treating rosacea by administering a reduced dose of minocycline, wherein said administration reduces the IGA score of the subject by at least one grade compared to the IGA score of placebo composition.

In an aspect of the above embodiments, the method of treating rosacea by administering a reduced dose of minocycline, wherein said administration reduces the IGA score of the subject by at least one grade compared to the IGA score about 1-16 weeks before the treatment.

In an aspect of the above embodiments, the method of treating rosacea by administering a reduced dose of minocycline, wherein said administration results in improved efficacy as assessed by the IGA score, in at least about 15%, 20%, 25%, 30%, 35%, 40%, 45%, 50%, 55%, 60%, 65%, 70% or 75% of the subjects as compared to the IGA score before the treatment.

In an aspect of the above embodiments, the method of treating rosacea by administering a reduced dose of minocycline, wherein said administration results in improved efficacy as assessed by the IGA score, in at least about 15% of the subjects as compared to the IGA score before the treatment.

In an aspect of the above embodiments, the method of treating rosacea by administering a reduced dose of minocycline, wherein said administration results in improved efficacy as assessed by the IGA score, in at least about 30% of the subjects as compared to the IGA score before the treatment.

In an aspect of the above embodiments, the method of treating rosacea by administering a reduced dose of minocycline, wherein said administration reduces the IGA score of the subject by at least one grade compared to the IGA score of an oral doxycycline composition comprising 40 mg of doxycycline.

In an aspect of the above embodiments, the method of treating rosacea by administering about 10 mg to about 40 mg of minocycline, wherein said administration reduces the IGA score to an equal or greater extent as compared to administration of an oral doxycycline composition comprising 40 mg of doxycycline.

In an aspect of the above embodiments, the method of treating rosacea by administering about 20 mg of minocycline, wherein said administration reduces the IGA score to an equal or greater extent as compared to administration of an oral doxycycline composition comprising 40 mg of doxycycline.

In an aspect of the above embodiments, the method of treating rosacea by administering about 30 mg to 40 mg of minocycline, wherein said administration reduces the IGA score of the subject by at least about 25%, about 50%, about 75% or about 100% compared to the IGA score of an oral doxycycline composition comprising 40 mg of doxycycline.

In an aspect of the above embodiments, the method of treating rosacea by administering about 30 mg to about 40 mg of minocycline, wherein said administration reduces the IGA score of the subject by at least about 25% compared to the IGA score of an oral doxycycline composition comprising 40 mg of doxycycline.

In an aspect of the above embodiments, the method of treating rosacea by administering about 40 mg of minocycline, wherein said administration reduces the IGA score of the subject by at least about 25%, about 50%, about 75% or about 100% compared to the IGA score of an oral doxycycline composition comprising 40 mg of doxycycline.

In an aspect of the above embodiments, the method of treating rosacea by administering about 40 mg of minocycline, wherein said administration reduces the IGA score of the subject by at least about 25% compared to the IGA score of an oral doxycycline composition comprising 40 mg of doxycycline.

In an aspect of the above embodiments, the method of treating rosacea by administering a reduced dose of minocycline, wherein said administration significantly reduced the severity of rosacea as compared to the severity of rosacea before the treatment, and wherein said severity of the rosacea is assessed counting a number of inflammatory lesions.

In an aspect of the above embodiments, the method of treating rosacea by administering a reduced dose of minocycline, wherein said administration significantly reduces the number of inflammatory lesions compared to the inflammatory lesions before the treatment.

In an aspect of the above embodiments, the method of treating rosacea by administering a reduced dose of minocycline, wherein said administration significantly reduces the number of inflammatory lesions compared to the inflammatory lesions of placebo composition.

In an aspect of the above embodiments, the method of treating rosacea by administering a reduced dose of minocycline, wherein said administration reduces the number of inflammatory lesions of the subject by at least about 15%, 20%, 25%, 30%, 35%, 40%, 45%, 50%, 55%, 60%, 65%, 70%, 75%, 80%, 85%, 90%, 95% or 100% as compared to the number of inflammatory lesions before the treatment.

In an aspect of the above embodiments, the method of treating rosacea by administering a reduced dose of minocycline, wherein said administration reduces the number of inflammatory lesions of the subject by at least about 15% as compared to the number of inflammatory lesions before the treatment.

In an aspect of the above embodiments, the method of treating rosacea by administering a reduced dose of minocycline, wherein said administration reduces the number of inflammatory lesions of the subject by at least about 30% as compared to the number of inflammatory lesions before the treatment.

In an aspect of the above embodiments, the method of treating rosacea by administering a reduced dose of minocycline, wherein said administration reduces the number of inflammatory lesions of the subject by at least about 50% as compared to the number of inflammatory lesions before the treatment.

In an aspect of the above embodiments, the method of treating rosacea by administering about 10 mg to about 40 mg of minocycline, wherein said administration significantly reduces the number of inflammatory lesions score to an equal or greater extent as compared to administration of an oral doxycycline composition comprising 40 mg of doxycycline.

In an aspect of the above embodiments, the method of treating rosacea by administering about 20 mg of minocycline, wherein said administration reduces the number of inflammatory lesions score to an equal or greater extent as compared to administration of an oral doxycycline composition comprising 40 mg of doxycycline.

In an aspect of the above embodiments, the method of treating rosacea by administering about 30 mg to about 40 mg of minocycline, wherein said administration reduces the inflammatory lesions by at least about 25%, about 50%, about 75% or about 100% compared to a number of inflammatory lesions of an oral doxycycline composition comprising 40 mg of doxycycline.

In an aspect of the above embodiments, the method of treating rosacea by administering about 30 mg to about 40 mg of minocycline, wherein said administration reduces the inflammatory lesions by at least about 50% compared to a number of inflammatory lesions of an oral doxycycline composition comprising 40 mg of doxycycline.

In an aspect of the above embodiments, the method of treating rosacea by administering about 30 mg to about 40 mg of minocycline, wherein said administration reduces the inflammatory lesions by at least about 75% compared to a number of inflammatory lesions of an oral doxycycline composition comprising 40 mg of doxycycline.

In an aspect of the above embodiments, the method of treating rosacea by administering about 30 mg to about 40 mg of minocycline, wherein said administration reduces the inflammatory lesions by at least about 100% compared to a number of inflammatory lesions of an oral doxycycline composition comprising 40 mg of doxycycline.

In an aspect of the above embodiments, the method of treating rosacea by administering about 40 mg of minocycline, wherein said administration reduces the inflammatory lesions by at least about 25%, about 50%, about 75% or about 100% compared to a number of inflammatory lesions of an oral doxycycline composition comprising 40 mg of doxycycline.

In an aspect of the above embodiments, the method of treating rosacea by administering about 40 mg of minocycline, wherein said administration reduces the inflammatory lesions by at least about 50% compared to a number of inflammatory lesions of an oral doxycycline composition comprising 40 mg of doxycycline.

In an aspect of the above embodiments, the method of treating rosacea by administering about 40 mg of minocycline, wherein said administration reduces the inflammatory lesions by at least about 75% compared to a number of inflammatory lesions of an oral doxycycline composition comprising 40 mg of doxycycline.

In an aspect of the above embodiments, the method of treating rosacea by administering about 40 mg of minocycline, wherein said administration reduces the inflammatory lesions by at least about 100% compared to a number of inflammatory lesions of an oral doxycycline composition comprising 40 mg of doxycycline.

In an aspect of the above embodiments, the present application relates to a method of treating an inflammatory skin condition by administering a pharmaceutical composition comprising a therapeutic effective amount of less than 45 mg dose of minocycline to a subject in need thereof, wherein said composition is administered orally.

In an aspect of the above embodiments, the present application relates to a method of treating rosacea by administering a pharmaceutical composition comprising a therapeutic effective amount of less than 45 mg dose of minocycline to a subject in need thereof, wherein said composition is administered orally.

In an aspect of the above embodiments, the present application relates to a method of treating acne by administering a pharmaceutical composition comprising a therapeutic effective amount of less than 45 mg dose of minocycline to a subject in need thereof, wherein said composition is administered orally.

In an aspect of the above embodiments, the present application relates to a method of treating rosacea by administering a pharmaceutical composition comprising about 40 mg dose of minocycline to a subject in need thereof, wherein said composition is administered orally.

In an aspect of the above embodiments, the present application relates to a method of treating rosacea by administering a pharmaceutical composition comprising about 35 mg dose of minocycline to a subject in need thereof, wherein said composition is administered orally.

In an aspect of the above embodiments, the present application relates to a method of treating rosacea by administering a pharmaceutical composition comprising about 30 mg dose of minocycline to a subject in need thereof, wherein said composition is administered orally.

In an aspect of the above embodiments, the present application relates to a method of treating rosacea by administering a pharmaceutical composition comprising about 25 mg dose of minocycline to a subject in need thereof, wherein said composition is administered orally.

In one embodiment, the present application relates to a method of treating rosacea by administering a pharmaceutical composition comprising about 20 mg dose of minocycline to a subject in need thereof, wherein said composition is administered orally.

In one embodiment, the present application relates to a method of treating rosacea by administering a pharmaceutical composition comprising about 15 mg dose of minocycline to a subject in need thereof, wherein said composition is administered orally.

In one embodiment, the present application relates to a method of treating rosacea by administering a pharmaceutical composition comprising about 10 mg dose of minocycline to a subject in need thereof, wherein said composition is administered orally.

In an aspect of the above embodiments, the pharmaceutical composition of present application is administered once daily.

In another embodiment, the present application relates to a method of treating rosacea by administering a pharmaceutical composition comprising a therapeutic effective amount of less than 45 mg dose of minocycline to a subject in need thereof, wherein said composition is administered once daily.

In an aspect of the above embodiments, the pharmaceutical composition of present application is administered twice daily.

In another embodiment, the present application relates to a method of treating rosacea by administering a pharmaceutical composition comprising a therapeutic effective amount of less than 45 mg dose of minocycline to a subject in need thereof, wherein said composition is administered twice daily.

In another aspect of the above embodiments, the pharmaceutical composition of present application is with or without food.

In another embodiments, the present application relates to a method of treating rosacea by administering a pharmaceutical composition comprising a therapeutic effective amount of less than 45 mg dose of minocycline to a subject in need thereof, wherein said composition is administered with or without food.

In an embodiment, the present application relates to a method of treating rosacea by administering an oral pharmaceutical composition comprising a reduced dose of minocycline to a subject in need thereof, wherein said method provides body-weight-independent dosing regimen for minocycline.

In an aspect of the above embodiments, the present application relates to a method of treating rosacea by administering a pharmaceutical composition comprising a therapeutic effective amount of less than 45 mg dose of minocycline to a subject in need thereof, wherein said composition is administered orally in the form of oral tablets, capsules, pills, minitablets, pellets, granules, powder, suspension, syrup and the like.

In an embodiment, the present application relates to a method of treating an inflammatory skin condition by administering a pharmaceutical composition comprising minocycline or a pharmaceutically acceptable salt thereof to a subject in need thereof, and measuring plasma concentration and/or interstitial fluid concentration of minocycline in the subject.

As will be recognized by one of ordinary skill in the art, depending on the circumstances, plasma concentration and/or interstitial fluid concentration of minocycline can be measured daily, more than daily, or less than daily during an entire course of treatment or a portion of a course of treatment of the subject. In some embodiments, for example, the subject can be measured for 1, 2, 3, 4, 5, 6, 7, 8, 9, 10, 11, 12, 13, 14, 15, or 16 weeks.

In some embodiments, the method can involve monitoring measurements until such time as a steady state maximum plasma and/or interstitial fluid concentration of minocycline in achieved and maintained for a defined period of time. In some embodiments, if a steady state of minocycline in achieved and maintained for a defined period of time, the dose of minocycline can be maintained for the duration of the course of treatment In some embodiments, the method can involve identifying the steady state maximum plasma concentration. In some embodiments, the method can further involve determining whether the steady state maximum plasma concentration is no greater than about 500 ng/ml.

As will be recognized by one of ordinary skill in the art, depending on the circumstances, it can be beneficial to make use of plasma concentration and/or interstitial fluid concentration of minocycline to determine a number of parameters. For example, in some embodiments, it can be useful to calculate fluctuation index, as defined herein. In some embodiments, it can be useful to monitor fluctuation index. In some embodiments, it can be useful to determine whether the fluctuation index is at about 1.0. In some embodiments, it can be useful to calculate any variation in fluctuation index from a first time point during treatment to one or more additional time points during treatment. In some embodiments, it can be useful to determine whether variation in the fluctuation index is less than about 30, 20, or 10%.

In an embodiment, the present application relates to a pharmaceutical composition comprising minocycline for treating an inflammatory skin condition in a subject in need thereof, wherein said composition is in the form of oral tablets, capsules, pills, minitablets, pellets, granules, powder, suspension or syrup.

In an embodiment, the present application relates to a pharmaceutical composition comprising minocycline for treating rosacea in a subject in need thereof, wherein said composition is in the form of oral tablets, capsules, pills, minitablets, pellets, granules, powder, suspension or syrup.

In an embodiment, the present application relates to a pharmaceutical composition comprising minocycline for treating acne in a subject in need thereof, wherein said composition is in the form of oral tablets, capsules, pills, minitablets, pellets, granules, powder, suspension or syrup.

In an aspect of the above embodiment, the pharmaceutical composition of minocycline is in the form of matrix-type compositions, wherein minocycline is distributed uniformly in the matrix of one or more pharmaceutically acceptable excipients.

In another aspect of the above embodiments, the pharmaceutical composition of minocycline is in the form of gastro-retentive system, wherein said system is designed to retain in stomach for prolonged time and release of minocycline to upper part of the gastrointestinal (GI) tract. Different approaches or systems to prolong the gastric residence time include mucoadhesive or bioadhesive systems, high density systems, expandable or swelling systems, and floating drug delivery systems, including gas generating systems.

In yet another aspect of the above embodiments, the pharmaceutical composition of minocycline is in the form of osmotic drug delivery system, wherein said system comprises minocycline layer with water swellable polymer (osmogen) and a push layer.

In another aspect of the above embodiments, the pharmaceutical composition of minocycline is in the form of modified release composition, wherein said composition comprises an immediate release (IR) portion and/or an extended release (ER) portion containing minocycline with one or more pharmaceutically acceptable excipients.

In an embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises an immediate release (IR) portion and/or an extended release (ER) portion containing minocycline with one or more pharmaceutically acceptable excipients.

In an aspect of the above embodiments, the pharmaceutical composition of present application comprises therapeutically effective amount of minocycline to a subject in need thereof.

In another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 0 to about 100 percent of minocycline in an immediate release (IR) portion; (ii) about 0 to about 100 percent minocycline in an extended release (ER) portion; and (iii) one or more pharmaceutically acceptable excipients.

In another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 0 to about 100 percent of minocycline in an immediate release (IR) portion; (ii) about 0 to about 100 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 0 to about 100 percent of minocycline in an immediate release (IR) portion; (ii) about 0 to about 100 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 30 percent of minocycline in an immediate release (IR) portion; (ii) about 70 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 25 percent of minocycline in an immediate release (IR) portion; (ii) about 75 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 20 percent of minocycline in an immediate release (IR) portion; (ii) about 80 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 40 percent of minocycline in an immediate release (IR) portion; (ii) about 60 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 50 percent of minocycline in an immediate release (IR) portion; (ii) about 50 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 60 percent of minocycline in an immediate release (IR) portion; (ii) about 40 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 70 percent of minocycline in an immediate release (IR) portion; (ii) about 30 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 75 percent of minocycline in an immediate release (IR) portion; (ii) about 25 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum plasma concentration of not more than about 500 ng/ml of minocycline; and said composition comprises (i) about 80 percent of minocycline in an immediate release (IR) portion; (ii) about 20 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 0 to about 100 percent of minocycline in an immediate release (IR) portion; (ii) about 0 to about 100 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 30 percent of minocycline in an immediate release (IR) portion; (ii) about 70 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 25 percent of minocycline in an immediate release (IR) portion; (ii) about 75 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 40 percent of minocycline in an immediate release (IR) portion; (ii) about 60 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 20 percent of minocycline in an immediate release (IR) portion; (ii) about 80 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 50 percent of minocycline in an immediate release (IR) portion; (ii) about 50 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 70 percent of minocycline in an immediate release (IR) portion; (ii) about 30 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 75 percent of minocycline in an immediate release (IR) portion; (ii) about 25 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 80 percent of minocycline in an immediate release (IR) portion; (ii) about 20 percent minocycline in an extended release (ER) portion; and (iii) one or more pharmaceutically acceptable excipients.

In yet another embodiment, the present application relates to a method of treating rosacea by administering a pharmaceutical composition comprising a therapeutically effective amount of minocycline to a subject in need thereof, wherein said administration results in a steady state maximum interstitial fluid concentration of not more than about 200 ng/ml of minocycline; and said composition comprises (i) about 60 percent of minocycline in an immediate release (IR) portion; (ii) about 40 percent minocycline in an extended release (ER) portion; and (iii) one or more pharmaceutically acceptable excipients In an aspect of the above embodiments, the immediate release (IR) and/or extended release (ER) portions are present in the form of a granule, pellet, bead, spherule, mini tablet, powder and the like or mixtures thereof.

In an embodiment, the present application relates to a process of preparing pharmaceutical composition comprising a therapeutically effective amount of minocycline.

In another embodiment, the present application relates to a process of preparing pharmaceutical composition comprising a therapeutically effective amount of less than 45 mg dose of minocycline, wherein said composition is administered orally.

In another aspect of the above embodiments, the process involves conventional methods to prepare oral pharmaceutical composition, that includes, but not limited to, wet or dry granulation, using fluidized bed granulator or high shear mixer granulator, direct compression, extrusion-spheronization, melt granulation/extrusion, spray-drying, spray-congealing, freeze-drying, or any other conventional process known in the art.

In an aspect of the above embodiments, the process involves coating or layering of minocycline over inert cores with coating or layering materials comprising minocycline and/or other suitable pharmaceutical excipients like binders, plasticizers or disintegrants over the inert cores.

The process of coating or layering includes any method known in the art such as, but not limited to, by spraying a suspension or dispersion of said coating material comprising minocycline, in a conventional coating pan or fluidized bed equipment (such as a Wurster or Glatt) followed by drying of cores. Alternatively, said coating materials may also be applied by powder-coating, wherein the cores are maintained in a sticky state, a mixture of coating material is added continuously or periodically so as to adhere to the sticky cores, followed by drying of coated cores when desired coating is achieved.

The "inert core" as used herein, refers to a pharmaceutically acceptable inert substrate which is routinely used in formulation art, that includes, but not limited to, powder or a multiparticulate such as a granule, a pellet, a bead, a spherule, a beadlet, a microcapsule, a millisphere, a nanocapsule, a nanosphere, a microsphere or a minitablet, which comprises at least one pharmaceutically acceptable excipient selected from the group comprising of water soluble, water insoluble, water swellable or water non swellable material such as starch, sugar, microcrystalline cellulose, vegetable gums, waxes, and the like.

The inert cores may also be prepared with the techniques known to a person skilled in the art, such as, wet granulation, dry granulation, or extrusion-spheronization and the like. The inert cores have a size of diameter in the range of about 125 to about 600 microns.

Suitable solvent(s) used in the preparation of minocycline solution are selected from, but not limited to, water, methanol, ethanol, n-propanol, isopropanol, dichloromethane, acetone, absolute alcohol and the like or mixtures thereof.

Suitable examples of binder(s) that may be used in the present application include, but are not limited to, methyl cellulose, hydroxy propyl cellulose, hydroxy propyl methyl cellulose, polyvinyl pyrrolidone, polyvinyl alcohol, propylene glycol, pre gelatinized starch, oxide such as polyethylene oxide and the like or mixtures thereof. The binders may be combination of two or more, such as hydroxy propyl cellulose and hydroxy propyl methyl cellulose. The binders used in the present application have a viscosity from about 5 centipoise to about 15 centipoise.

In another aspect of the above embodiments, the extended release (ER) portion are prepared by coating the immediate release (IR) portion with one or more release modifying polymers.

In another aspect of the above embodiments, the present application relates to a process of preparing pharmaceutical composition of minocycline comprising extended release (ER) portion, wherein the ER coating layer has a thickness of not more than 200 μm.

Suitable examples of release modifying polymers that may be used in the present application include, but are not limited to, unsubstituted alkyl celluloses or cellulose ethers like ethyl cellulose; and substituted alkyl celluloses or cellulose ethers like hydroxy alkyl celluloses and carboxy alkyl celluloses such as hydroxy ethyl cellulose, hydroxy propyl cellulose, hydroxy propyl methyl cellulose, carboxy methyl ethyl cellulose and carboxy methyl cellulose; acrylic and methacrylic acid polymers and copolymers such as methyl methacrylate, ethoxy ethyl methacrylates, ethyl acrylate, amino alkyl methacrylate copolymer, poly(acrylic acid), poly(methacrylic acid), polyacrylamide and glycidyl methacrylate copolymers; polyalkylene oxides such as polyethylene oxide and polypropylene oxide and copolymers of ethylene oxide and propylene oxide; poly vinyl alcohols, gums, synthetic resins and the like or mixtures thereof. The release modifying polymers may be present in amounts ranging from about 5% to about 45% w/w of the composition.

In another embodiment, the pharmaceutical composition of minocycline of present application may comprises one or more pharmaceutically acceptable excipient(s) selected from lubricants, glidants, anti-tacking agents, plasticizers, disintegrants or opacifying agents and the like or mixtures thereof.

The lubricant, glidant or anti-tacking agent may be used interchangeably in the composition of the present application and are selected from, but not limited to, metallic stearates such as magnesium stearate, calcium stearate, zinc stearate; stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, colloidal silicon dioxide, magnesium trisilicate, powdered cellulose, starch, tribasic calcium phosphate and the like or mixtures thereof. The amount of such agents may range from about 0.1% w/w to about 10% w/w of the composition.

The plasticizer used in the pharmaceutical composition of the present application may be used in the coating layer to increase the flexibility and strength of the coat/layer, and suitable plasticizer may be selected from, but not limited to, propylene glycol, polyethylene glycol, triethyl citrate, acetyl triethyl citrate, diethyl phthalate, dibutyl phthalate, dibutyl sebacate, tributyl citrate or mixtures thereof. The plasticizer may be present in amounts ranging from about 0.1% to about 20% w/w of the composition.

The disintegrant used in the pharmaceutical composition of the present application may be selected from, but not limited to, crospovidone, sodium starch glycolate, croscarmellose sodium, croscarmellose potassium, croscarmellose calcium, carboxymethylcellulose, pregelatinized starch, carboxymethyl starch and the like or mixtures thereof. The disintegrant may be present in amount from 1% to 20% by weight of the composition.

In an aspect of the above embodiments, the present process of preparing pharmaceutical composition comprising about 10 mg to about 40 mg dose of minocycline comprises steps of: (i) preparing an immediate release (IR) portion; and/or (ii) preparing an extended release (ER) portion; (iii) combining the IR and/or ER portions with one or more pharmaceutically acceptable excipient(s); and (iv) filling the mixture of (iii) into a capsule or compressed into a tablet.

In an aspect of the above embodiments, the present process of preparing pharmaceutical composition comprising less than 45 mg dose of minocycline comprises steps of: (i) preparing an immediate release (IR) portion; and/or (ii) preparing an extended release (ER) portion; (iii) combining the IR and/or ER portions with one or more pharmaceutically acceptable excipient(s); and (iv) filling the mixture of (iii) into a capsule or compressed into a tablet. In an aspect of the above embodiments, the process comprises combining the IR and ER portions in a ratio of about 0:100, about 10:90, about 20:80, about 30:70, about 40:60, about 50:50, about 60:40, about 70:30, about 75:25, about 80:20, about 90:10 or about 100:0.

In an aspect of the above embodiments, the present process of preparing pharmaceutical composition comprising less than 45 mg dose of minocycline comprises steps of: (i) preparing an immediate release (IR) portion; and/or (ii) preparing an extended release (ER) portion; (iii) combining the IR and/or ER portions in a ratio of about 0:100 to about 100:0 with one or more pharmaceutically acceptable excipient(s); and (iv) filling the mixture of (iii) into a capsule or compressed into a tablet.

In an aspect of the above embodiments, the present process of preparing pharmaceutical composition comprising less than 45 mg dose of minocycline comprises steps of: (i) preparing an immediate release (IR) portion; and/or (ii) preparing an extended release (ER) portion; (iii) combining the IR and ER portions in a ratio of about 20:80 with one or more pharmaceutically acceptable excipient(s); and (iv) filling the mixture of (iii) into a capsule or compressed into a tablet.

In an aspect of the above embodiments, the present process of preparing pharmaceutical composition comprising less than 45 mg dose of minocycline comprises steps of: (i) preparing an immediate release (IR) portion; and/or (ii) preparing an extended release (ER) portion; (iii) combining the IR and ER portions in a ratio of about 25:75 with one or more pharmaceutically acceptable excipient(s); and (iv) filling the mixture of (iii) into a capsule or compressed into a tablet.

In an aspect of the above embodiments, the present process of preparing pharmaceutical composition comprising less than 45 mg dose of minocycline comprises steps of: (i) preparing an immediate release (IR) portion; and/or (ii) preparing an extended release (ER) portion; (iii) combining the IR and ER portions in a ratio of about 30:70 with one or more pharmaceutically acceptable excipient(s); and (iv) filling the mixture of (iii) into a capsule or compressed into a tablet.

In an aspect of the above embodiments, the present process of preparing pharmaceutical composition comprising less than 45 mg dose of minocycline comprises steps of: (i) preparing an intragranular portion; and/or (ii) preparing an extragranular portion; (iii) mixing (i) and (ii) with suitable pharmaceutically acceptable excipients, (iv) compressing the mixture of (iii) into a tablet; and (v) optionally coating tablet of (iv) using suitable coating material.

In an embodiment, the pharmaceutical composition comprising minocycline can also be co-administered (simultaneously or sequentially) with one or more pharmaceutical agents of value in the form of commercially available dosage forms or which can be developed in a suitable pharmaceutically acceptable dosage forms for treating an inflammatory skin condition or related disease conditions In another embodiment, the pharmaceutical composition comprising minocycline can be subjected to dissolution studies in 500 ml of pH 2.1 simulated gastric fluid, pH 4.5 acetate buffer and pH 6.8 phosphate buffer, with USP Type I apparatus at a speed of 100 rpm and 37° C. till 3 hours.

Examples of the pharmaceutical agents that can be co-administered are selected from, but not limited to, systemic and topical antibiotics like tetracycline, minocycline, doxycycline, metronidazole, erythromycin and clindamycin; or retinoids like tretinoin (vitamin A or retinoic acid), isotretinoin (13-cis-retinoic acid), acitretin and the like or a mixtures thereof.

The present application is further illustrated by the examples which are provided merely to be exemplary of the pharmaceutical composition described above and do not limit the scope of the application. Certain modifications and equivalents will be apparent to those skilled in the art and are intended to be included within the scope of the present application. The present invention is illustrated below by reference to the following examples. However, one skilled in the art will appreciate that the specific methods and results discussed are merely illustrative of the present invention, and not to be construed as limiting the application. The following examples may include compilations of data that are representative of data gathered at various times during the course of development and experimentation related to the present invention.

EXAMPLES

Example 1-5

Pharmaceutical compositions were prepared including 40 mg, 30 mg, 20 mg, or 10 mg of minocycline. Further details regarding exemplary compositions used for these non-limiting examples are set forth in Table 1.

TABLE 1

| Composition | Ex-1 (eq. to Minocycline 40 mg) | Ex-2 (eq. to Minocycline 30 mg) | Ex-3 (eq. to Minocycline 20 mg) | Ex-4 (eq. to Minocycline 10 mg) | Ex-5 (eq. to Minocycline 40 mg) |
|---|---|---|---|---|---|
| (% w/w) | | | | | |
| Drug loading | | | | | |
| Inert core | 25.6 | 25.6 | 25.6 | 25.6 | — |
| Minocycline Hydrochloride | 24.9 | 24.9 | 24.9 | 24.9 | 24.9 |
| Hydroxy propyl cellulose | 10.4 | 10.4 | 10.4 | 10.4 | — |
| Hydroxy propyl methyl cellulose | | | | | |
| Microcrystalline cellulose | — | — | — | — | 41.05 |
| Polyethylene glycol 400 | 1.3 | 1.3 | 1.3 | 1.3 | — |
| Talc | 3.6 | 3.6 | 3.6 | 3.6 | — |
| Water | Quantity sufficient | Quantity sufficient | Quantity sufficient | Quantity sufficient | Quantity sufficient |
| Barrier coating | | | | | |
| Hydroxy propyl methyl cellulose | 3.3 | 3.3 | 3.3 | 3.3 | 3.3 |
| Polyethylene glycol 400 | 0.33 | 0.33 | 0.33 | 0.33 | 0.33 |
| Talc | 0.98 | 0.98 | 0.98 | 0.98 | 0.98 |
| Water | Quantity sufficient | Quantity sufficient | Quantity sufficient | Quantity sufficient | Quantity sufficient |
| Release modifying coating | | | | | |
| Ethyl cellulose | 9.24 | 9.24 | 9.24 | 9.24 | 9.24 |
| Hydroxy propyl methyl cellulose | 3.0 | 3.0 | 3.0 | 3.0 | 3.0 |
| Triethyl citrate | 0.92 | 0.92 | 0.92 | 0.92 | 0.92 |
| Talc | 3.7 | 3.7 | 3.7 | 3.7 | 3.7 |
| Isopropyl alcohol | Quantity sufficient | Quantity sufficient | Quantity sufficient | Quantity sufficient | Quantity sufficient |
| Water | Quantity sufficient | Quantity sufficient | Quantity sufficient | Quantity sufficient | Quantity sufficient |
| Outer top coating | | | | | |
| Hydroxy propyl methyl cellulose | 7.48 | 7.48 | 7.48 | 7.48 | 7.48 |
| Polyethylene glycol 400 | 0.74 | 0.74 | 0.74 | 0.74 | 0.74 |
| Talc | 2.24 | 2.24 | 2.24 | 2.24 | 2.24 |
| Water | Quantity sufficient | Quantity sufficient | Quantity sufficient | Quantity sufficient | Quantity sufficient |
| Lubrication | | | | | |
| Outer top coated portions | 80.4 | 80.4 | 80.4 | 80.4 | 80.4 |
| Barrier coated portions | 17.6 | 17.6 | 17.6 | 17.6 | 17.6 |
| Talc | 1.96 | 1.96 | 1.96 | 1.96 | 1.96 |
| Total | 100 | 100 | 100 | 100 | 100 |

Procedure:

Exemplary compositions can be prepared using the following procedure.

a. With regard to exemplary compositions 1-4, as set forth in Table 1, a drug dispersion was prepared by mixing minocycline hydrochloride, hydroxy propyl methyl cellulose, hydroxy propyl cellulose, polyethylene glycol and talc in water and layered onto inert core to obtain drug loaded pellets.

b. With regard to exemplary composition 5, as set forth in Table 1, drug and microcrystalline cellulose were wet granulated. The wet mass was then extruded and the extrudates were spheronized to prepare drug pellets.

c. A barrier coating solution was prepared by dissolving hydroxy propyl methyl cellulose, followed by adding polyethylene glycol and talc with stirring.

d. A release modifying coating solution was prepared by dissolving the required amount of ethyl cellulose and hydroxy propyl methyl cellulose in isopropyl alcohol, followed by adding triethyl citrate.

e. An immediate release (IR) portion was prepared by coating the barrier coating solution as prepared in step (c) onto a drug loaded portion of step (a) or step (b).

f. An extended release (ER) portion was prepared by coating the release modifying coating solution as prepared in step (d) onto the drug loaded portion of step (a) or step (b), followed by an outer top or seal coating.

g. A required quantity of the outer top coated portions and the barrier coated portions were mixed with talc and filled into a required size of empty hard gelatine capsule shells and packaged in a suitable pharmaceutical storage bottle.

Example 6

An exemplary pharmaceutical composition comprising minocycline was prepared as set forth in Table 2.

TABLE 2

| Composition | % w/w |
|---|---|
| Drug loaded portion-1 | |
| Minocycline Hydrochloride (eq. to Minocycline 40 mg) | 5.3 |
| Microcrystalline Cellulose | 10.6 |
| Hydroxypropyl cellulose LF | 0.3 |
| Polyethylene Oxide | 0.5 |
| Cross carmellose sodium | 0.3 |
| Sodium stearyl fumarate | 0.001 |
| Drug loaded release modifying and bio-adhesive portion-2 | |
| Minocycline Hydrochloride | 16.0 |
| Microcrystalline Cellulose | 13.3 |
| Hydroxypropyl methyl cellulose | 13.3 |
| Polyethylene Oxide | 39.9 |
| Cross carmellose sodium | 0.5 |
| Sodium stearyl fumarate | 0.026 |
| Total | 100.0 |

Procedure:

Exemplary compositions can be prepared using the following procedure.

a. The noted amounts of minocycline hydrochloride, microcrystalline cellulose, hydroxypropyl cellulose, polyethylene oxide and cross carmellose sodium were sifted through suitable sieve.

b. The blend of step (a) was lubricated using sodium stearyl fumarate to prepare bioadhesive portion.

c. Required amount of minocycline hydrochloride, microcrystalline cellulose, hydroxypropyl methyl cellulose, polyethylene oxide and cross carmellose sodium were sifted through suitable sieve.

d. The blend of step (c) was lubricated using sodium stearyl fumarate to prepare release modifying portion.

e. The lubricated blend of step (b) was compressed on top of drug loaded release modifying and bio-adhesive portion into bi-layered tablets.

Example 7-8

Exemplary pharmaceutical compositions comprising minocycline weres prepared as set forth in Table 3.

TABLE 3

| Composition | % w/w | |
|---|---|---|
| | Example-7 | Example-8 |
| Intragranular portion | | |
| Minocycline Hydrochloride (eq. to Minocycline 40 mg) | 10.3 | 28.1 |
| Microcrystalline Cellulose | 50.0 | 21.1 |
| Polyethylene oxide | — | 17.6 |
| Hydroxypropyl methyl cellulose | 26.9 | 7.0 |
| Isopropyl alcohol: Water | Quantity sufficient | Quantity sufficient |
| Exragranular portion | | |
| Microcrystalline Cellulose | 10.5 | 17.6 |
| Colloidal Silicon Dioxide | 0.8 | 1.1 |
| Sodium Stearyl Fumarate | 1.5 | 1.1 |
| Outer top coating | | |
| Hydroxypropyl methyl cellulose | — | 4.6 |
| Talc | — | 1.4 |
| Polyethylene Glycol | — | 0.5 |
| Water | — | q.s. |
| Total | 100 | 100 |

Procedure:

Exemplary compositions can be prepared using the following procedure.

a. Required amount of minocycline hydrochloride, microcrystalline cellulose and/or polyethylene oxide were sifted through suitable sieve.

b. Required amount of microcrystalline cellulose, colloidal silicon dioxide and sodium stearyl fumarate were sifted through suitable sieve.

c. Solution of hydroxypropyl methylcellulose was prepared in a mixture of isopropyl alcohol and water.

d. The powder mass of step (a) was granulated with the solution of step (c).

e. Granules of step (d) were dried in suitable dryer and dried granules are passed through suitable sieve.

f. Example 7: Dried granules of step (e) were lubricated by mixing with powder mass of step (b) and compressed into tablets.

g. Example 8: Dried granules of step (e) were lubricated by mixing with powder mass of step (b) and compressed into tablets followed by coating with outer top coating composition as mentioned in Examples 1-5.

Example 9

The pharmacokinetic parameters for pharmaceutical compositions as shown in Examples 1 and 3 were studied by using an open-label, 6-cohort pharmacokinetic study. The study was conducted in total 24 healthy human subjects in 6 groups, randomized to receive a single dose of composition of examples 1 and 3; and ORACEA®—40 mg doxycycline capsules orally. The subjects were received the treatments at day 1, followed by sampling, and continued to self-administer it for next 19 days. At steady state level on day 21, the subjects were supervised for dosing followed by sampling and check-out 24 hours later. The sampling in plasma and interstitial fluid is performed and the results are shown in following table 4, table 5, table 6, table 7 and table 8.

TABLE 4

(Plasma sample)

| Parameters | Day 1 | | | Day 21 | | |
|---|---|---|---|---|---|---|
| | Ex-1 | Ex-3 | ORACEA ® | Ex-1 | Ex-3 | ORACEA ® |
| $C_{max}$ (ng/ml) | 382.83 | 130.68 | 405.86 | 337.74 | 164.46 | 701.85 |
| $C_{min}$ (ng/ml) | 3.29 | 4.01 | 5.2 | 96.96 | 35.11 | 38.96 |
| $C_{avg}$ (ng/ml) | 187.43 | 73.53 | 211 | 210.01 | 95.76 | 44.62 |
| $AUC_{0-t}$ (ng * hr/ml) | 3549.64 | 1412.31 | 4377.52 | 3957.62 | 1953.92 | 6074.76 |
| $T_{max}$ (hr) | 1.75 | 1.75 | 1.75 | 1.50 | 1.50 | 1.50 |

TABLE 5

(Fluctuation index at steady state in plasma sample)

| | Day 21 | | | | | | | | |
|---|---|---|---|---|---|---|---|---|---|
| | Ex-1 | | | Ex-3 | | | ORACEA ® | | |
| Parameters | Mean | SD* | % CV | Mean | SD | % CV | Mean | SD | % CV |
| $C_{max}$ (ng/ml) | 337.74 | 95.45 | 28.26 | 164.46 | 70.87 | 43.09 | 701.85 | 534.2 | 76.11 |
| $AUC_{0-t}$ (ng * hr/ml) | 3957.62 | 1099 | 27.77 | 1953.92 | 645.8 | 33.05 | 6074.76 | 1980 | 32.59 |
| Fluctuation index** | | 1.15 | | | 1.35 | | | 1.51 | |

*SD—Standard deviation

**Fluctuation index - $[(C_{max} - C_{min})/C_{avg}]$

TABLE 6

(Variations in plasma sample)

| | % Variations from day 1 to day 21 | | |
|---|---|---|---|
| Parameters | Ex-1 | Ex-3 | ORACEA ® |
| $C_{max}$ (ng/ml) | −12% | 21% | 42% |
| $AUC_{0-t}$ (ng * hr/ml) | 11% | 28% | 28% |
| Fluctuation index | 14% | 57% | 59% |

TABLE 7

(Interstitial fluid sample)

| Parameters | Day 1 | | | Day 21 | | |
|---|---|---|---|---|---|---|
| | Ex-1 | Ex-3 | ORACEA ® | Ex-1 | Ex-3 | ORACEA ® |
| $C_{max}$ (ng/ml) | 109.68 | 42.94 | 81.52 | 125.69 | 60.64 | 114.69 |
| $C_{min}$ (ng/ml) | 2.8 | 1.2 | 0.8 | 39.9 | 16.4 | 33.3 |
| $C_{avg}$ (ng/ml) | 63.6 | 26.3 | 49.5 | 76.9 | 37.1 | 26.6 |
| $AUC_{0-t}$ (ng * hr/ml) | 1412.29 | 589.89 | 1088.55 | 1604.77 | 877.82 | 1573.63 |
| $T_{max}$ (hr) | 3.00 | 3.50 | 4.00 | 3.00 | 4.00 | 4.00 |

TABLE 8

(ratio of interstitial fluid to plasma samples)

| | Interstitial fluid to plasma ratios (%) | | | | | |
|---|---|---|---|---|---|---|
| | Ex-1 | | Ex-2 | | ORACEA ® | |
| Parameters | Day 1 | Day 21 | Day 1 | Day 21 | Day 1 | Day 21 |
| $AUC_{0-t}$ (ng * hr/ml) | 40 | 41 | 42 | 45 | 25 | 26 |
| $C_{avg}$ (ng/ml) | 34 | 37 | 36 | 39 | 23 | 22 |

Example 10

The pharmaceutical compositions as shown in Example 1 and 3 were studied in a 16-week, multi-center, randomized, double-blind, parallel-group, controlled study to evaluate efficacy. Subjects, who were at least 18 years old, diagnosed with papulopustular rosacea were randomized to 4 different treatment groups (50 subjects each in groups 1 to 4). Each subject was allocated to one of the treatment groups, receiving a single dose of Example 1 (Group 1) and Example 3 (Group 2); ORACEA®—40 mg doxycycline capsules (Group 3); and placebo capsules (Group 4), orally for 16 weeks. Subjects' visits were scheduled at screening, baseline (day 1), and weeks 4, 8, 12 and 16.

Figure 3:
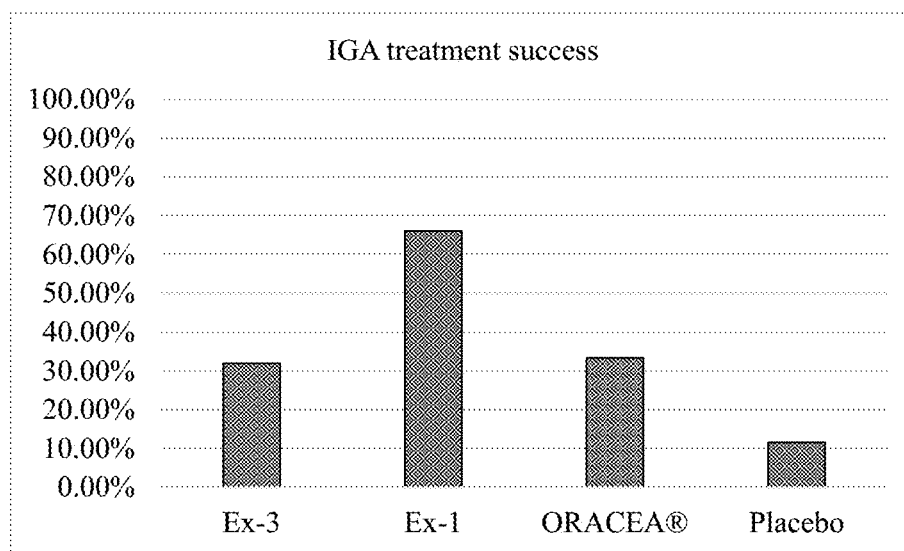
FIG. 3 shows IGA "treatment success" for Example 1, Example 3, ORACEA® and placebo, when subjected to a 16-week, multi-center, randomized, double-blind, parallel-group, controlled study.
Figure 4:
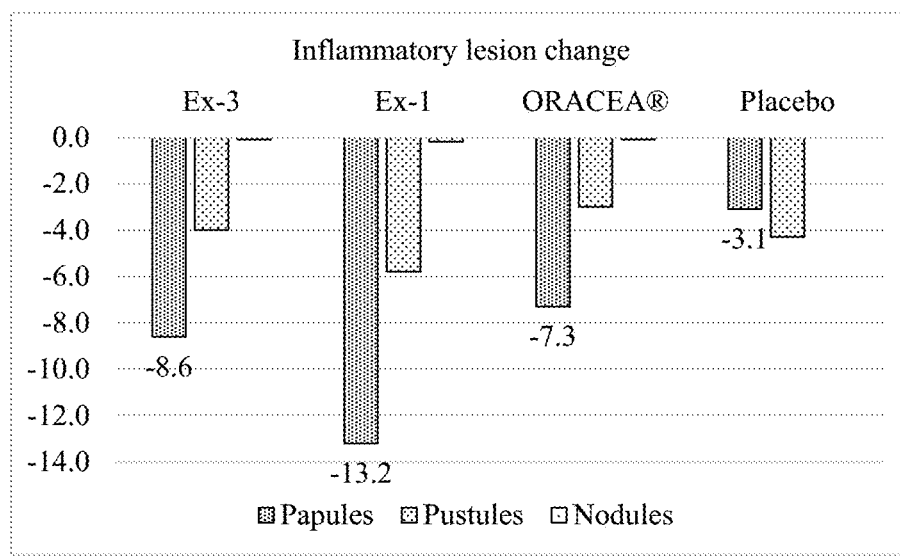
FIG. 4 shows change in lesion nos. for papules, pustules and nodules for Example 1, Example 3, ORACEA® and placebo, when subjected to a 16-week, multi-center, randomized, double-blind, parallel-group, controlled study.
Figure 5:
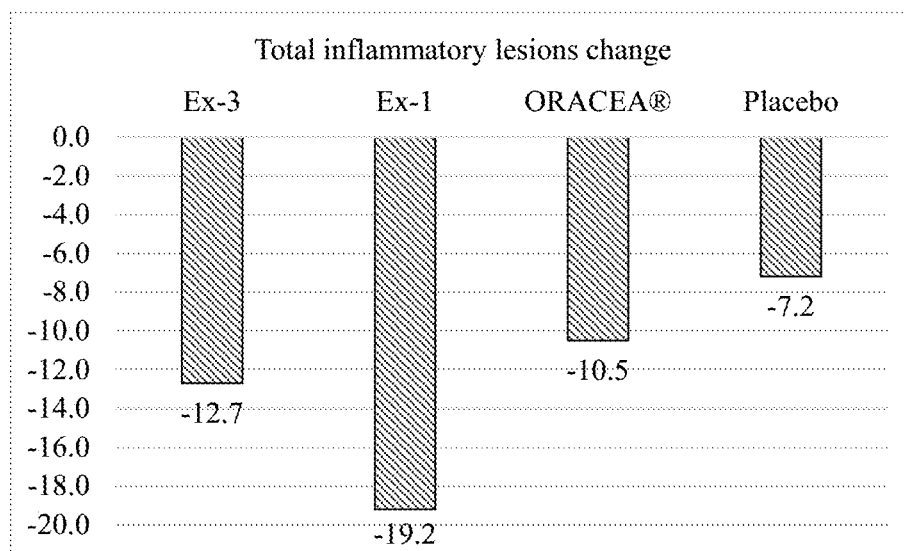
FIG. 5 shows change in total inflammatory lesions for Example 1, Example 3, ORACEA® and placebo, when subjected to a 16-week, multi-center, randomized, double-blind, parallel-group, controlled study.

Clinical assessments of efficacy was conducted based on, proportion of subjects with IGA 'treatment success (reduction in IGA grade)' and reduction in total inflammatory lesion count (sum of papules, pustules, and nodules) from baseline (day 1) to weeks 4, 8, 12 and 16. The results are shown in following table 9 (IGA 'treatment success), table 10 (total inflammatory lesion change), table 11 (P values) and FIG. 3, FIG. 4, FIG. 5.

TABLE 9

| Subject population | IGA 'treatment success' N (%) |
|---|---|
| Example 1 N = 53 | 35 (66.04%) |
| Example 3 N = 47 | 15 (31.91%) |
| ORACEA® N = 48 | 16 (33.33%) |
| Placebo N = 52 | 6 (11.54%) |

TABLE 10

| Subject population | Papules change in lesion no. (SD*) | Pustules change in lesion no. (SD*) | Nodules change in lesion no. (SD*) | Total inflammatory lesion change (SD) |
|---|---|---|---|---|
| Example 1 N = 53 | −13.2 (7.94) | −5.8 (6.16) | −0.2 (0.48) | −19.2 (9.73) |
| Example 3 N = 47 | −8.6 (9.10) | −4.0 (7.8) | −0.1 (0.50) | −12.7 (12.80) |
| ORACEA® N = 48 | −7.3 (11.44) | −3.0 (7.89) | −0.1 (0.62) | −10.5 (15.20) |
| Placebo N = 52 | −3.1 (7.92) | −4.3 (6.02) | 0.2 (1.21) | −7.2 (10.06) |

* SD—Standard deviation %

TABLE 11

| | P values | |
|---|---|---|
| Parameters | IGA 'treatment success' | Total inflammatory lesion change |
| Example 1 vs. Placebo | <0.0001 | <0.0001 |
| Example 3 vs. Placebo | 0.0133 | 0.0246 |
| Example 1 vs. ORACEA® | 0.0010 | 0.0004 |
| Example 1 vs. Example 3 | 0.0007 | 0.0076 |
| Example 3 vs. ORACEA® | 0.8828 | 0.3781 |

We claim:

1. A method of treating rosacea in a subject in need thereof, comprising administering an oral pharmaceutical composition comprising a body-weight independent dose of about 10 mg to about 40 mg of minocycline to a subject in need thereof, wherein the said composition results in a maximum plasma concentration ($C_{maxP}$) of about 55 ng/ml to about 450 ng/ml of minocycline, wherein said composition provides equivalent or improved efficacy as compared to the oral doxycycline composition comprising 40 mg of doxycycline, wherein said composition reduces the IGA score of the subject by at least one grade compared to the IGA score before treatment and wherein said composition reduces the number of inflammatory lesions of the subject by at least about 60% as compared to the number of inflammatory lesions before treatment.

2. The method of claim 1, wherein said composition comprises about 20 mg of minocycline.

3. The method of claim 1, wherein said composition comprises about 40 mg of minocycline.

4. The method of claim 1, wherein said rosacea is selected from the group consisting of: a papulopustular rosacea, an erythematotelangiectatic rosacea, a phymatous rosacea, an ocular rosacea, acne rosacea, a pyoderma faciale, a rosacea conglobata, a mild rosacea, a moderate rosacea, a severe rosacea, a mild to moderate rosacea, and a moderate to severe rosacea.

5. The method of claim 1, wherein said administration reduces the IGA score to an equal or greater extent as compared to administration of an oral doxycycline composition comprising 40 mg of doxycycline.

6. The method of claim 1, wherein said administration reduces the number of inflammatory lesions to an equal or greater extent as compared to administration of an oral doxycycline composition comprising 40 mg of doxycycline.

7. The method of claim 1, wherein said composition, upon oral administration for about 3 weeks or less, exhibits a fluctuation index ($FI_{SSP}$) of about 0.9 to about 1.3 in plasma.

8. The method of claim 1, wherein said composition upon oral administration for about 3 weeks or less, exhibits at least one of the following pharmacokinetic parameters, when measured in plasma samples:
a) $C_{maxSSP}/D$ of about 5 ng/ml/mg to about 12 ng/ml/mg; and
b) $AUC_{0-tSSP}/D$ of about 60 ng/ml/mg to about 114 ng/ml/mg.

9. The method of claim 1, wherein said composition upon oral administration for about 3 weeks or less, exhibits a ratio of minocycline exposure in interstitial fluid to plasma ($AUC_{0-tSSIF}/AUC_{0-tSSP}$) of at least about 10% higher, as compared to oral administration of a doxycycline composition comprising 40 mg of doxycycline.

10. The method of claim 1, wherein said composition, upon oral administration for about 3 weeks or less, exhibits at least about a 30% lower fluctuation index ($FI_{SSP}$)

$[(C_{maxSSP}-C_{minSSP})/C_{avgSSP}]$ in plasma, as compared to oral administration of a doxycycline composition comprising 40 mg of doxycycline.

11. The method of claim 1, wherein said composition, upon oral administration for about 3 weeks or less, exhibits a $C_{maxSSP}$ of at least about 10% lower, as compared to oral administration of a doxycycline composition comprising 40 mg of doxycycline.

12. The method of claim 1, wherein said composition, upon oral administration for about 3 weeks or less, exhibits at least about a 10% reduction in a coefficient of variance (CV %) of $C_{maxSSP}$, as compared to oral administration of a doxycycline composition comprising 40 mg of doxycycline.

13. The method of claim 1, wherein said composition, upon oral administration for about 3 weeks or less, exhibits at least about a 10% reduction in a coefficient of variance (CV %) of minocycline exposure ($AUC_{0-tSSP}$) in plasma, as compared to oral administration of a doxycycline composition comprising 40 mg of doxycycline.

14. The method of claim 1, wherein said composition, upon oral administration for about 3 weeks or less, exhibits a plasma concentration ratio ($C_{maxSSP}$:$C_{maxP}$) of at least about 30% lower, as compared to oral administration of a doxycycline composition comprising 40 mg of doxycycline.

15. The method of claim 1, wherein said composition, upon oral administration for about 3 weeks or less, exhibits a plasma concentration ratio ($C_{maxSSP}$:$C_{maxP}$) of at least about 0.9.

16. The method of claim 1, wherein said composition, upon oral administration for about 3 weeks or less, exhibits a $C_{avgSSP}$ of at least about 20% lower, as compared to oral administration of a doxycycline composition comprising 40 mg of doxycycline.

17. The method of claim 1, wherein said composition exhibits a Cmax in the subject's plasma at about 1.75 hours after administration.

18. The method of claim 1, wherein said composition upon administration exhibits a $C_{maxSSP}$ of minocycline of not more than about 500 ng/ml.

* * * * *